US007798955B2

(12) United States Patent
Ishihara et al.

(10) Patent No.: US 7,798,955 B2
(45) Date of Patent: Sep. 21, 2010

(54) IMAGE GENERATING DEVICE FOR GENERATING A FLUORESCENCE IMAGE

(75) Inventors: Yasushige Ishihara, Hachioji (JP); Toshiaki Watanabe, Hachioji (JP)

(73) Assignee: Olympus Corporation, Tokyo (JP)

( * ) Notice: Subject to any disclaimer, the term of this patent is extended or adjusted under 35 U.S.C. 154(b) by 1241 days.

(21) Appl. No.: 11/258,964

(22) Filed: Oct. 26, 2005

(65) Prior Publication Data
US 2006/0089554 A1 Apr. 27, 2006

(30) Foreign Application Priority Data
Oct. 26, 2004 (JP) ............................. 2004-311313
Oct. 27, 2004 (JP) ............................. 2004-312847

(51) Int. Cl.
*A61B 1/00* (2006.01)
(52) U.S. Cl. ...................... 600/101; 600/109; 250/230; 250/234; 250/235; 359/197; 359/201; 359/202; 359/368; 73/105
(58) Field of Classification Search ................. 600/101, 600/109; 250/230, 234, 235; 359/197, 201, 359/202, 368; 73/105
See application file for complete search history.

(56) References Cited

U.S. PATENT DOCUMENTS 5,131,744 A * 7/1992 Kaneko et al. ............... 356/138

FOREIGN PATENT DOCUMENTS

| JP | 06-125911 A | 5/1994 |
|---|---|---|
| JP | 07-163572 A | 6/1995 |
| JP | 07-204156 A | 8/1995 |
| JP | 08-224208 | 9/1996 |
| JP | 08-252218 | 10/1996 |
| JP | 10-151104 | 6/1998 |
| JP | 2001-147398 A | 5/2001 |
| JP | 2004-194821 A | 7/2004 |

OTHER PUBLICATIONS

Japanese Official Action dated Apr. 13, 2010.
Japanese Official Action dated Apr. 20, 2010.

* cited by examiner

*Primary Examiner*—Brian Casler
*Assistant Examiner*—John F Ramirez
(74) *Attorney, Agent, or Firm*—Scully, Scott, Murphy & Presser, P.C.

(57) ABSTRACT

Excitation light $\lambda$ex is two-dimensionally scanned onto the living body tissue in the form of condensed light using an x-axis scanning mirror, a y-axis scanning mirror, and a condenser lens, whereby the excitation light $\lambda$ex is cast onto the living body tissue. This allows fluorescence observation with a relatively low output intensity of a laser light source. Furthermore, a white light image is generated by scanning the white light in the same way, thereby enabling fluorescence observation in the same observation region and at the same timing as with normal observation. This enables fluorescence observation of a sufficient area which allows the user to distinguish living body tissues in an endoscope observation image while suppressing deterioration in the laser light source.

11 Claims, 31 Drawing Sheets

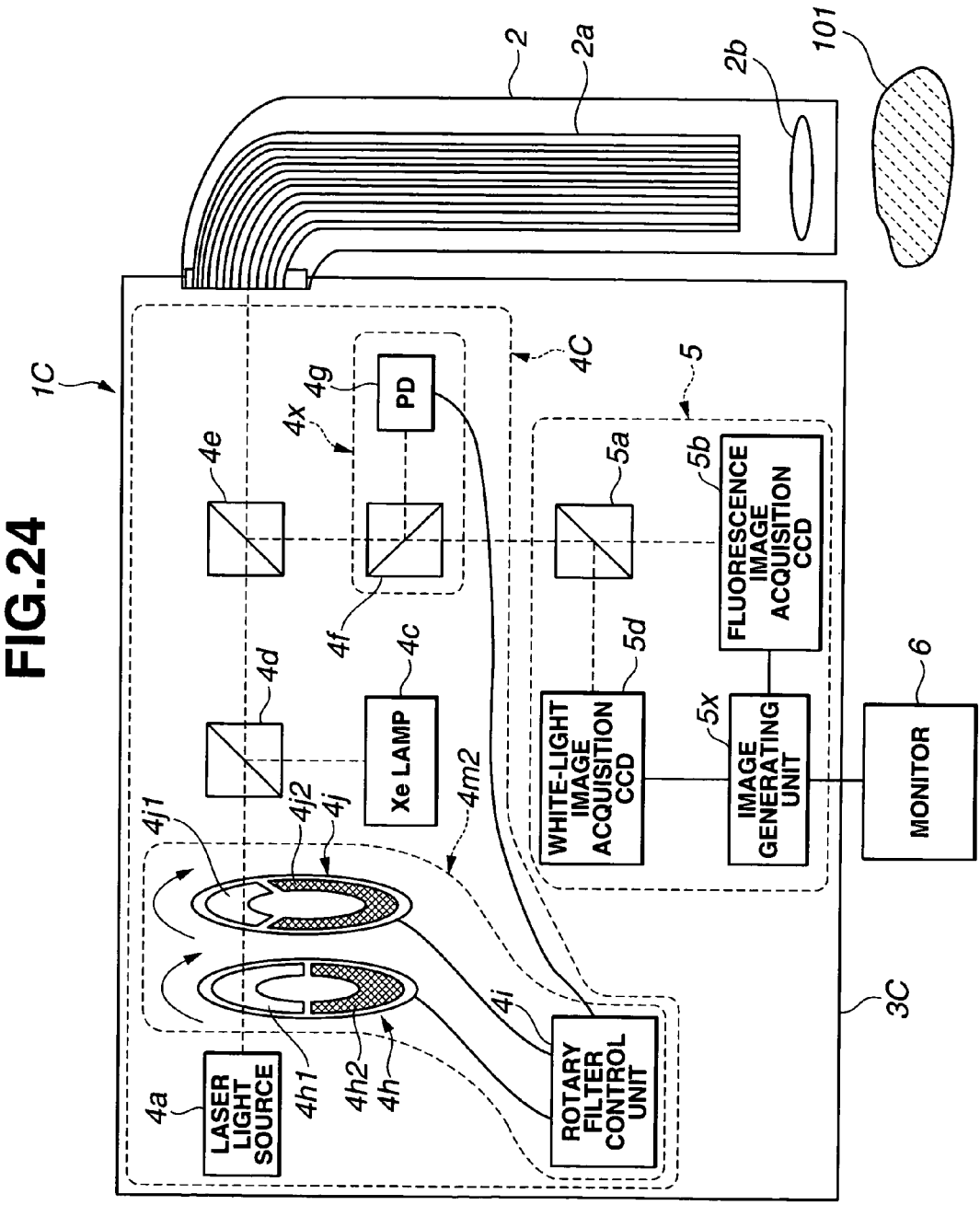

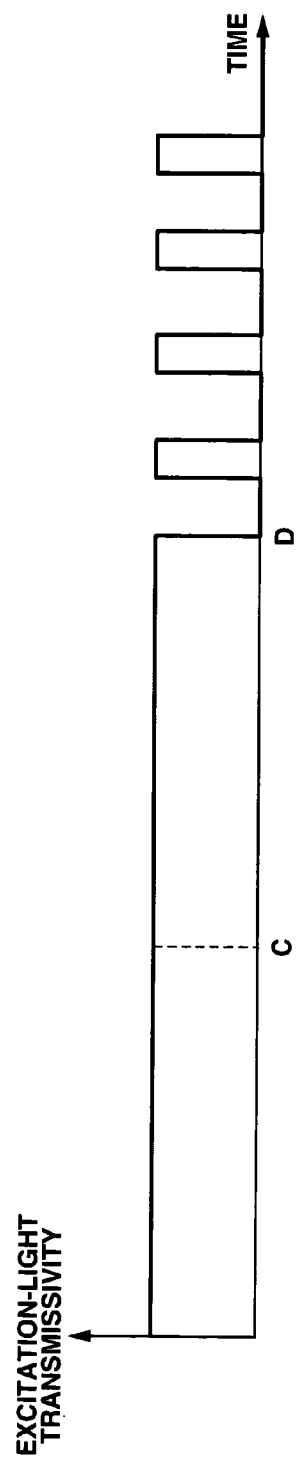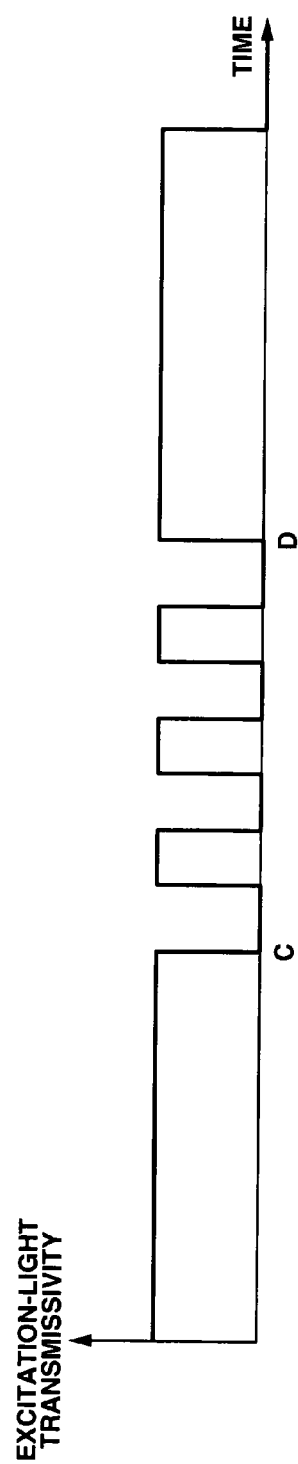

IMAGE GENERATING DEVICE FOR GENERATING A FLUORESCENCE IMAGE

This application claims benefit of Japanese Application No. 2004-311313 filed in Japan on Oct. 26, 2004, and Japanese Application No. 2004-312847 filed in Japan on Oct. 27, 2004, the contents of which are incorporated by this reference.

BACKGROUND OF THE INVENTION

1. Field of the Invention

The present invention relates to an image generating device, and particularly to an image generating device for generating a fluorescence image from fluorescence emitted by the subject due to excitation light cast on the subject.

2. Description of the Related Art

In recent years, diagnostic techniques are known in which self-fluorescence emitted from living body or fluorescence emitted from chemicals injected to the living body is detected and represented as a two-dimensional image. Such a fluorescence image assists in the diagnosis of degeneration of the living body tissue or the state of disease (e.g., the kind of disease, infiltrating area) such as cancer and so forth.

The living body tissue which receives excitation light emits fluorescence with a longer wavelength than that of the excitation light. Examples of fluorescent materials contained in the living body include: NADH (nicotinamide adenine dinucleotide); FMN (flavin mononucleotide); pyridine nucleotide; and so forth. Recently, the relation between such living-body-originated-materials and disease has come to be better understood. On the other hand, HpD (hematoporphyrin), Photofrin, ALA ($\delta$-amino levulinic acid), are readily accumulated in cancer tissue. This allows diagnosis of disease tissue by observing the fluorescence emitted from the aforementioned material injected into the living body.

For example, a technique is disclosed in Japanese Unexamined Patent Application Publication No. 8-252218, in which exciting laser light is output from the distal end of a light guide of an endoscope for fluorescence observation.

SUMMARY OF THE INVENTION

An image generating device according to the present invention comprises: an excitation light emission unit for emitting excitation light with a predetermined wavelength; a white light source for emitting white light; a first light introducing unit for introducing the excitation light to a subject; a second light introducing unit for introducing the white light to the subject; an excitation light scanning unit for scanning the excitation light introduced by the second light introducing unit onto a predetermined region within an illumination region in the subject to which the white light is introduced; a light condensing unit disposed between the excitation light scanning unit and the subject for condensing the excitation light onto the subject; a reflected white light photoreceptor unit for receiving the reflected light due to the white light from the subject; and a fluorescence photoreceptor unit for receiving fluorescence excited in the subject due to the excitation light.

Other features and advantages of the present invention will become apparent from the following description.

BRIEF DESCRIPTION OF THE DRAWINGS

FIG. 1 is a configuration diagram which shows a configuration of a fluorescence observation endoscope device;

FIG. 2 is a configuration diagram which shows a configuration of a modification 1 of the fluorescence observation endoscope device shown in FIG. 1;

FIG. 3 is a configuration diagram which shows a configuration of a modification 2 of the fluorescence observation endoscope device shown in FIG. 1;

FIG. 4 is a configuration diagram which shows a configuration of a modification 3 of the fluorescence observation endoscope device shown in FIG. 1; and FIG. 5 is a diagram for describing the operations of the fluorescence observation endoscope device shown in FIG. 4.

FIG. 6 is a configuration diagram which shows a fluorescence observation endoscope device;

FIG. 7 is a diagram for describing the functions of the fluorescence observation endoscope device shown in FIG. 6;

FIG. 8 is a configuration diagram which shows a configuration of a modification of the fluorescence observation endoscope device shown in FIG. 6; and FIG. 9 is a diagram for describing the functions of the fluorescence observation endoscope device shown in FIG. 7.

FIG. 10 is a configuration diagram which shows a fluorescence observation endoscope device;

FIG. 11 is a first diagram for describing the functions of the fluorescence observation endoscope device shown in FIG. 10;

FIG. 12 is a second diagram for describing the functions of the fluorescence observation endoscope device shown in FIG. 10;

FIG. 13 is a third diagram for describing the functions of the fluorescence observation endoscope device shown in FIG. 10; and FIG. 14 is a fourth diagram for describing the functions of the fluorescence observation endoscope device shown in FIG. 10;

FIGS. 15 through 34 relate to an embodiment 4 according to the present invention.

FIG. 15 is an overall configuration diagram which shows an image generating device according to the embodiment 4;

FIG. 16 is a diagram which shows change with time passage in the luminous intensity of the reflected light of the excitation light detected by a PD (photodiode) included in the image generating device according to the embodiment 4;

FIG. 17 is a diagram which shows the operation of the image generating device according to the embodiment 4 for controlling the luminous intensity of the laser light for handling a situation in which the change in the luminous intensity of the reflected excitation light over time has been detected as shown in FIG. 16;

FIG. 18 is a diagram which shows a threshold set for handling a situation in which the luminous intensity of the reflected excitation light changes over time as shown in FIG. 16;

FIG. 19 is a diagram for describing the operation of the image generating device according to the embodiment 4 for controlling the luminous intensity of the laser light using the threshold set as shown in FIG. 18;

FIG. 20 is a diagram for describing another control operation than that shown in FIG. 19;

FIG. 21 is a diagram which shows a configuration of the distal end of the scope of the image generating device according to a modification of the embodiment 4;

FIG. 22 is a diagram which shows a configuration of each component included in a device for forming an image in an image generating device according to a first modification of the embodiment 4;

FIG. 23 is a diagram which shows a configuration of an image generating device according to a second modification of the embodiment 4;

FIG. 24 is a diagram which shows a configuration of an image generating device according to a third modification of the embodiment 4;

FIG. 25 is a diagram which shows change of the transmissivity by actions of rotation of a first rotary filter included in the image generating device according to the third modification of the embodiment 4;

FIG. 26 is a diagram which shows change of the transmissivity by actions of rotation of a second rotary filter included in the image generating device according to the third modification of the embodiment 4;

FIG. 27 is a diagram which shows a configuration of an image generating device according to a fourth modification of the embodiment 4;

FIG. 28 is a diagram which shows change in the transmissivity due to rotation of one rotary filter included in the image generating device according to the fourth modification of the embodiment 4;

FIG. 29 is a diagram which shows an example of change in the transmissivity due to rotation of the other rotary filter included in the image generating device according to the fourth modification of the embodiment 4;

FIG. 30 is a diagram which shows change in the transmissivity achieved by actions of a combination of the rotary filters each of which achieves change in transmissivity as shown in FIGS. 28 and 29;

FIG. 31 is a diagram which shows another example than that shown in FIG. 29, and which also shows change in the transmissivity due to rotation of the other rotary filter included in the image generating device according to the fourth modification of the embodiment 4;

FIG. 32 is a diagram which shows change in the transmissivity achieved by actions of a combination of the rotary filters each of which achieves change in transmissivity as shown in FIGS. 28 and 31;

FIG. 33 is a diagram which shows a configuration of an image generating device according to a fifth modification of the embodiment 4; and FIG. 34 is a diagram which shows a configuration of an image generating device according to a sixth modification of the embodiment 4.

FIG. 35 is an overall configuration diagram which shows an image generating device according to the embodiment 5; and FIG. 36 is a diagram which shows an internal configuration of a device main unit and a probe of the image generating device according to the embodiment 5.

FIG. 37 is an overall configuration diagram which shows an image generating device according to the embodiment 6;

FIG. 38 is a diagram which shows an internal configuration of the distal end of an insertion unit of an endoscope included in the image generating device according to the embodiment 6;

FIG. 39 is a diagram which shows an example of the calculation result of the damping time constant calculated by a damping time calculating unit;

FIG. 40 is a diagram which shows another example than that shown in FIG. 39, and which also shows the calculation result of the damping time constant calculated by the damping time calculating unit; and FIG. 41 is a flowchart which shows the control operation performed by the image generating device according to the embodiment 6.

DETAILED DESCRIPTION OF THE PREFERRED EMBODIMENTS

Embodiment 1

Figure 1:
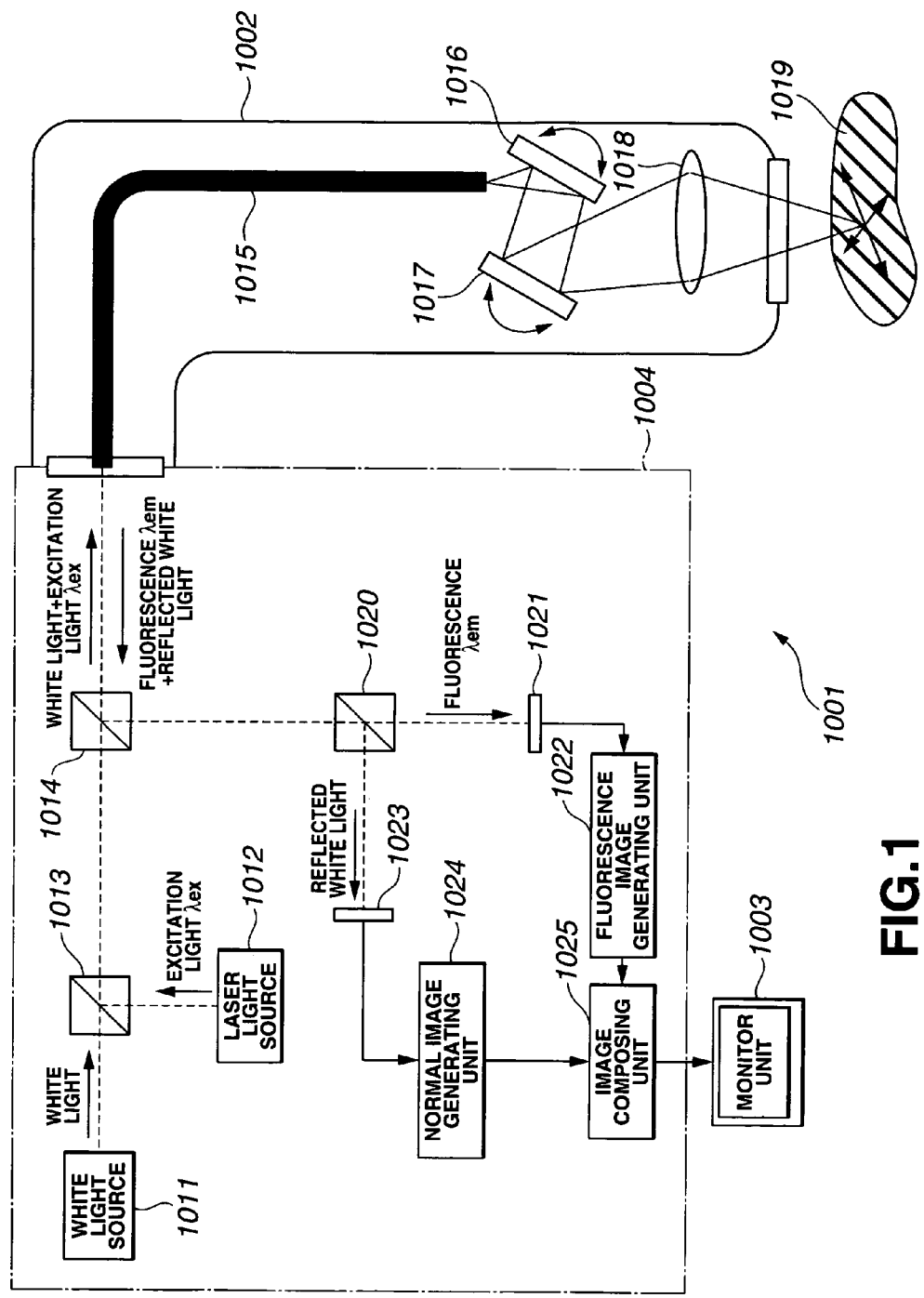
FIGS. 1 through 5 relate to an embodiment 1 according to the present invention.

As shown in FIG. 1, a fluorescence endoscope image generating device 1001 comprises an insertion unit 1002 for being inserted into the body cavity for acquiring an image of living body tissue therewithin, and an observation processing device 1004 for capturing and processing the living body tissue image acquired by the insertion unit 1002 and displaying the living body tissue image on a monitor unit 1003 as well as supplying excitation light and white light to the insertion unit 1002.

The observation processing device 1004 includes a white-light light source 1011 for emitting white light and a laser light source 1012 for emitting excitation light $\lambda$ex. Here, the white light is used for acquiring a normal observation image of the living body tissue. On the other hand, the excitation light is used to excite fluorescence (self-fluorescence emitted from the living body tissue and fluorescence emitted from chemicals) in the living body tissue.

With such a configuration, the white light cast from the white light source 1011 and the excitation light $\lambda$ex cast from the laser light source 1012 are introduced to the same optical path via a half mirror 1013, and are introduced into a single optical fiber 1014 inserted into the insertion unit 1002 through a half mirror 1014. The illumination light (excitation light $\lambda$ex and white light) cast from the single optical fiber 1015 is two-dimensionally scanned via an x-axis scanning mirror 1016 which is turned around a predetermined axis, and a y-axis scanning mirror 1017 which is turned around an axis orthogonal to the turning axis of the x-axis scanning mirror 1016.

The light (excitation light $\lambda$ex and white light) two-dimensionally scanned by the x-axis scanning mirror 1016 and the y-axis scanning mirror 1017 is cast onto a living body tissue 1019 through a condenser lens 1018. That is to say, the excitation light and the white light are two-dimensionally scanned on a predetermined normal endoscope observation region in the living body tissue 1019.

Then, the returned light (fluorescence $\lambda$em and reflected white light) returned from the living body tissue 1019 is introduced into the single optical fiber 1015 along the reverse optical path through the condenser lens 1018, the x-axis scanning mirror 1016, and the y-axis scanning mirror 1017. The light thus introduced into the single optical fiber 1015 is separated from the optical path for the illumination light (excitation light $\lambda$ex and white light) by the half mirror 1014. Furthermore, the returned light (fluorescence $\lambda$em and reflected white light) is separated into the fluorescence $\lambda$em and the reflected white light by the half mirror 1020.

The image of fluorescence $\lambda$em separated by the half mirror 1020 is captured by a PMT 1021 for fluorescence observation. The captured image signal from the PMT 1021 is subjected to signal processing at a fluorescence image generating unit 1022, thereby generating a fluorescence image of the living body tissue 1019.

On the other hand, the reflected white light separated by the half mirror 1020 is captured by a PD 1023 for normal observation. The captured signal from the PD 1023 is subjected to signal processing at a normal image generating unit 1024, thereby generating a normal image of the living body tissue 1019.

The fluorescence image and the normal image are generated using the same scanning mechanism, i.e., the x-axis scanning mirror 1016 and the y-axis scanning mirror 1017 for two-dimensional scanning. Thus, the fluorescence image and the normal image are acquired with the same scanning area and the same scanning timing. Then, an image composing unit 1025 composes the normal image generated by the normal image generating unit 1024 and the fluorescence image generated by the fluorescence image generating unit 1022 into a single image with the same timing. Thus, the monitor unit 1003 displays the composite image in which the fluorescence image has been superimposed on the normal image.

As described above, with the present embodiment, the excitation light $\lambda$ex is cast onto the living body tissue 1019 in the form of converted light two-dimensionally scanned by actions of a scanning mechanism formed of the x-axis scanning mirror 1016 and the y-axis scanning mirror 1017, and a condensing optical system formed of the condenser lens 1018. Thus, the present embodiment does not require a laser light source 1012 with a high output intensity. That is to say, the present embodiment enables fluorescence observation using the laser light source 1012 with a low output intensity. Furthermore, with the present embodiment, the images are acquired by scanning the excitation light $\lambda$ex and the white light using the same scanning mechanism. This allows fluorescence observation with the same observation region and with the same acquisition timing as with normal observation. Thus, the present embodiment enables fluorescence observation with a wide observation region in the same way as with normal observation while suppressing deterioration in the laser light source.

Note that the present embodiment is not restricted to the arrangement shown in FIG. 1. Modifications 1 through 3 perform the same operation and have the same advantages as with the present embodiment.

Modification 1 of the Embodiment 1

Figure 2:
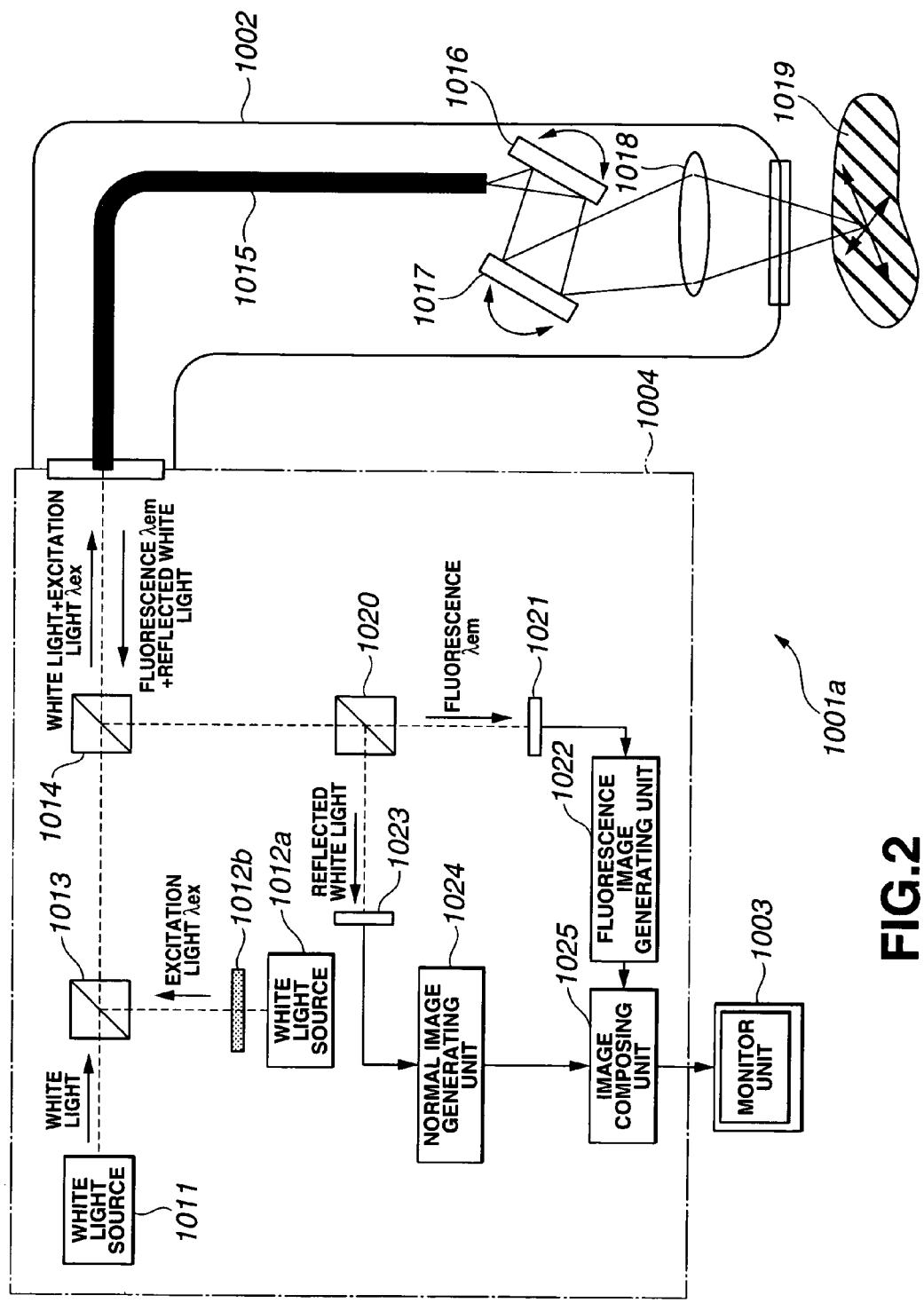

As shown in FIG. 2, a fluorescence endoscope image generating device 1001a according to a modification 1 of the present embodiment has generally the same configuration as that of the present embodiment (FIG. 1), except for including a white light source 1012a and a transmission filter 1012b which allows light with a wavelength of $\lambda$ex alone to pass therethrough, instead of the laser light source 1012. With the modification 1, the excitation light $\lambda$ex is extracted from the white light cast by the white light source 1012a by the transmission filter 1012b. The excitation light $\lambda$ex thus extracted is introduced into the half mirror 1013.

Modification 2 of the Embodiment 1

Figure 3:
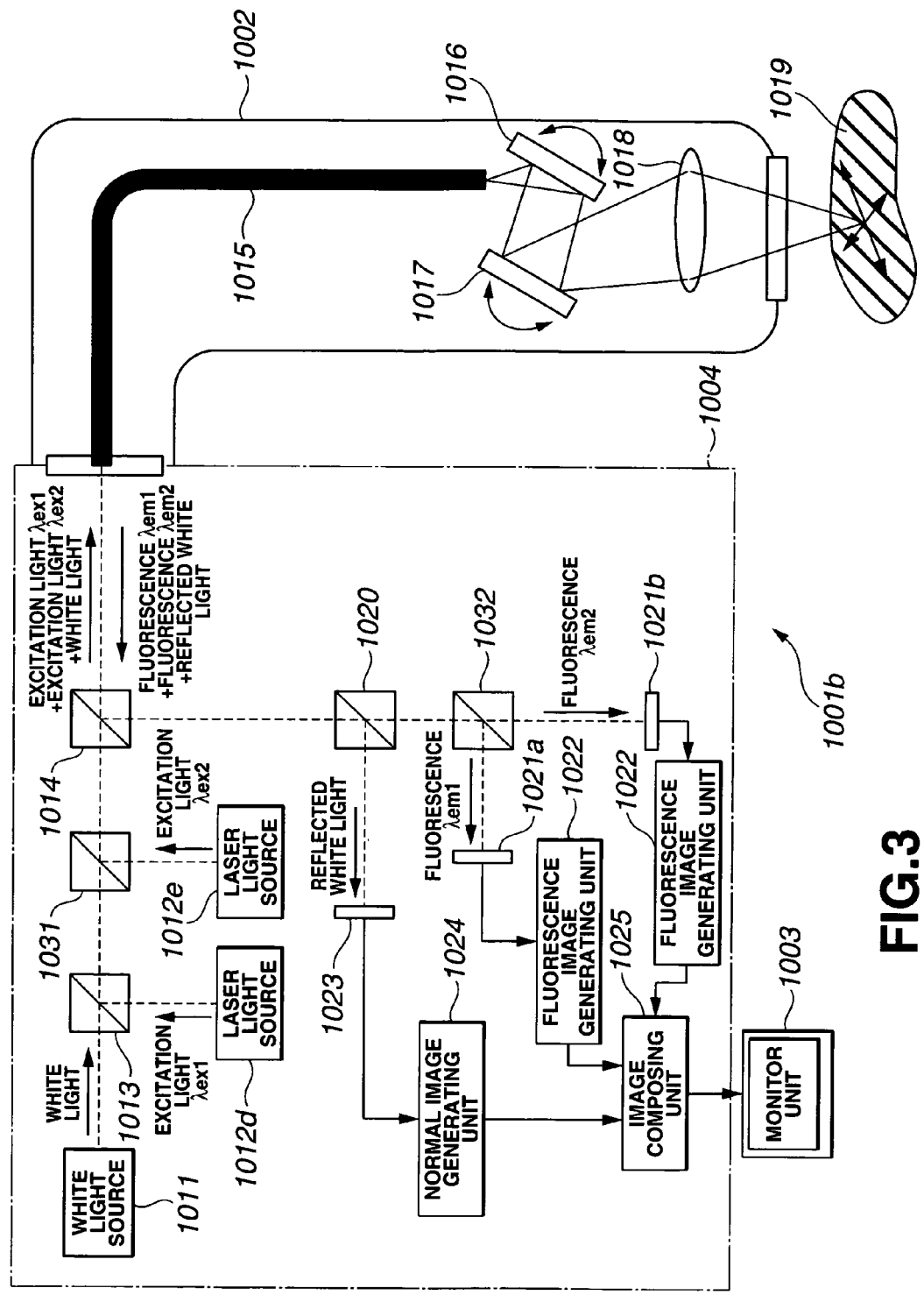

As shown in FIG. 3, a fluorescence endoscope image generating device 1001b according to a modification 2 of the present embodiment has generally the same configuration as that of the present embodiment (FIG. 1), except for including a first laser light source 1012d for the emission of first excitation light $\lambda$ex1 and a second laser light source 1012e for the emission of second excitation light $\lambda$ex2, instead of the laser light source 1012 according to the present embodiment (FIG. 1). With such a configuration, the first excitation light $\lambda$ex1 is introduced into the same optical path as the white light via the half mirror 1013 in the same way as with the present embodiment (FIG. 1). Furthermore, the second excitation light $\lambda$ex2 is introduced into the same optical path as the white light via a half mirror 1031. Furthermore, the second modification includes: a half mirror 1032 for separating fluorescence introduced via the half mirror 1020 into first fluorescence $\lambda$em1 excited by the first excitation light $\lambda$ex1 and second fluorescence $\lambda$em2 excited by the second excitation light $\lambda$ex2; a PMT 1021a for capturing the first fluorescence $\lambda$em1; and a PMT 1021b for capturing the second fluorescence $\lambda$em2. The present embodiment enables observation using two kinds of fluorescent dyes which emit fluorescence at different wavelengths at the same time.

Modification 3 of Embodiment 1

Figure 4:
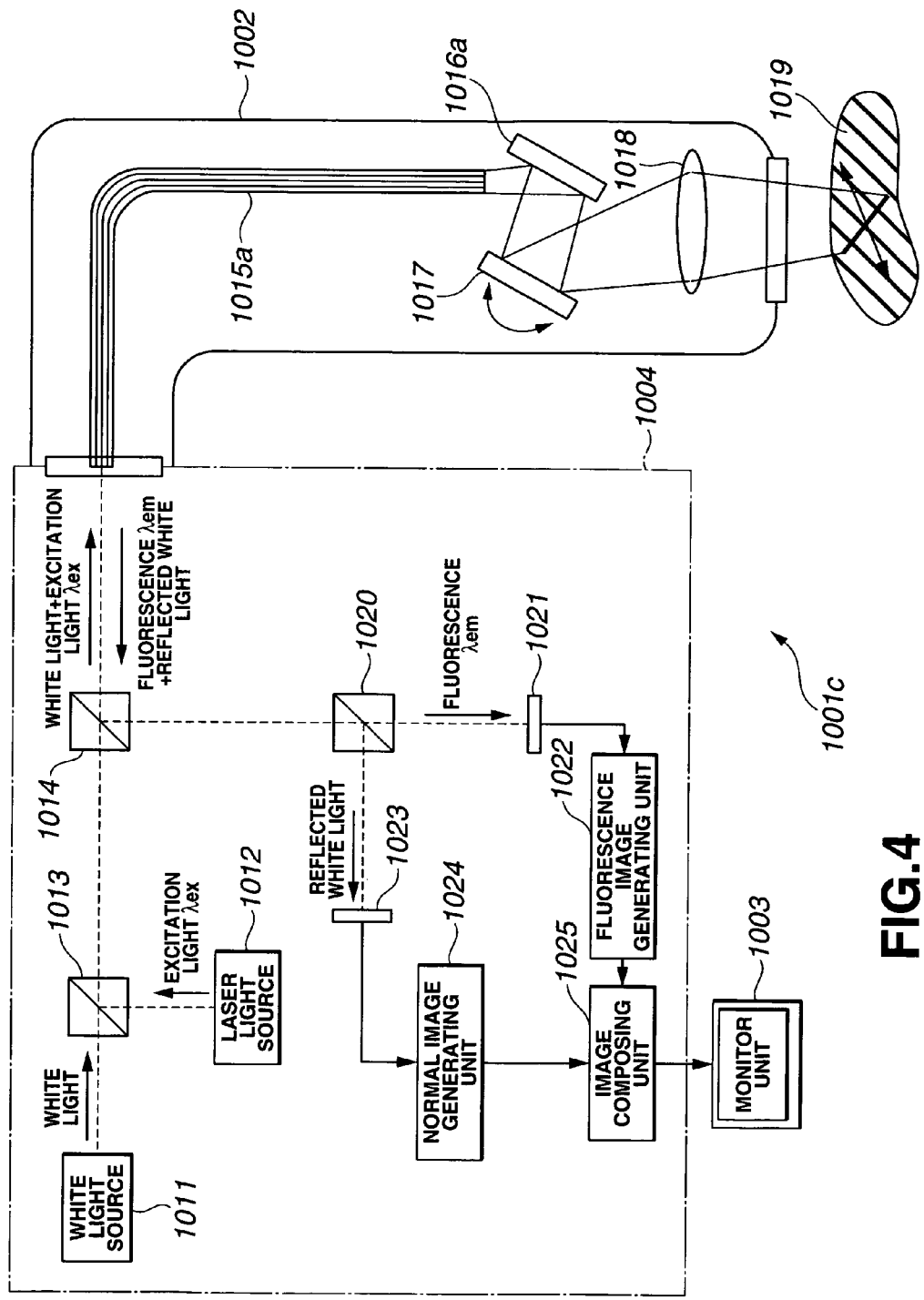
Figure 5:
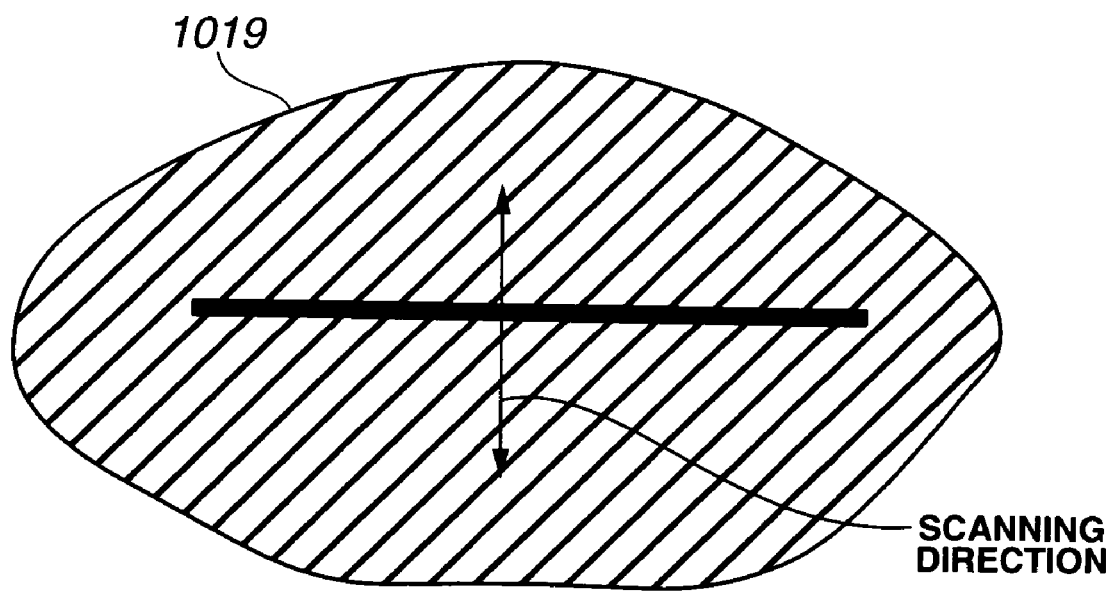

As shown in FIG. 4, a fluorescence endoscope image generating device 1001c according to a modification 3 of the present embodiment has generally the same configuration as that of the present embodiment (FIG. 1) except for including a linear optical fiber bundle 1015a instead of the single optical fiber 1015. Note that the linear optical fiber bundle 1015a is formed of multiple single optical fibers arrayed in line. With such a configuration, either of the x-axis scanning mirror 1016 or the y-axis scanning mirror 1017 forming the scanning mechanism, e.g., the x-axis scanning mirror 1016 may be replaced with a fixed mirror 1016a. As shown in FIG. 5, the present modification has the same functions and advantages as with the present embodiment simply by the scanning of the excitation light $\lambda$ex and white light cast on the living body tissue 1019 in a single line only.

Embodiment 2

An embodiment 2 has generally the same configuration as that of the embodiment 1. Accordingly, description will be made regarding only components that differ between these embodiments. On the other hand, the same components are denoted by the same reference numerals, and description thereof will be omitted.

Figure 6:
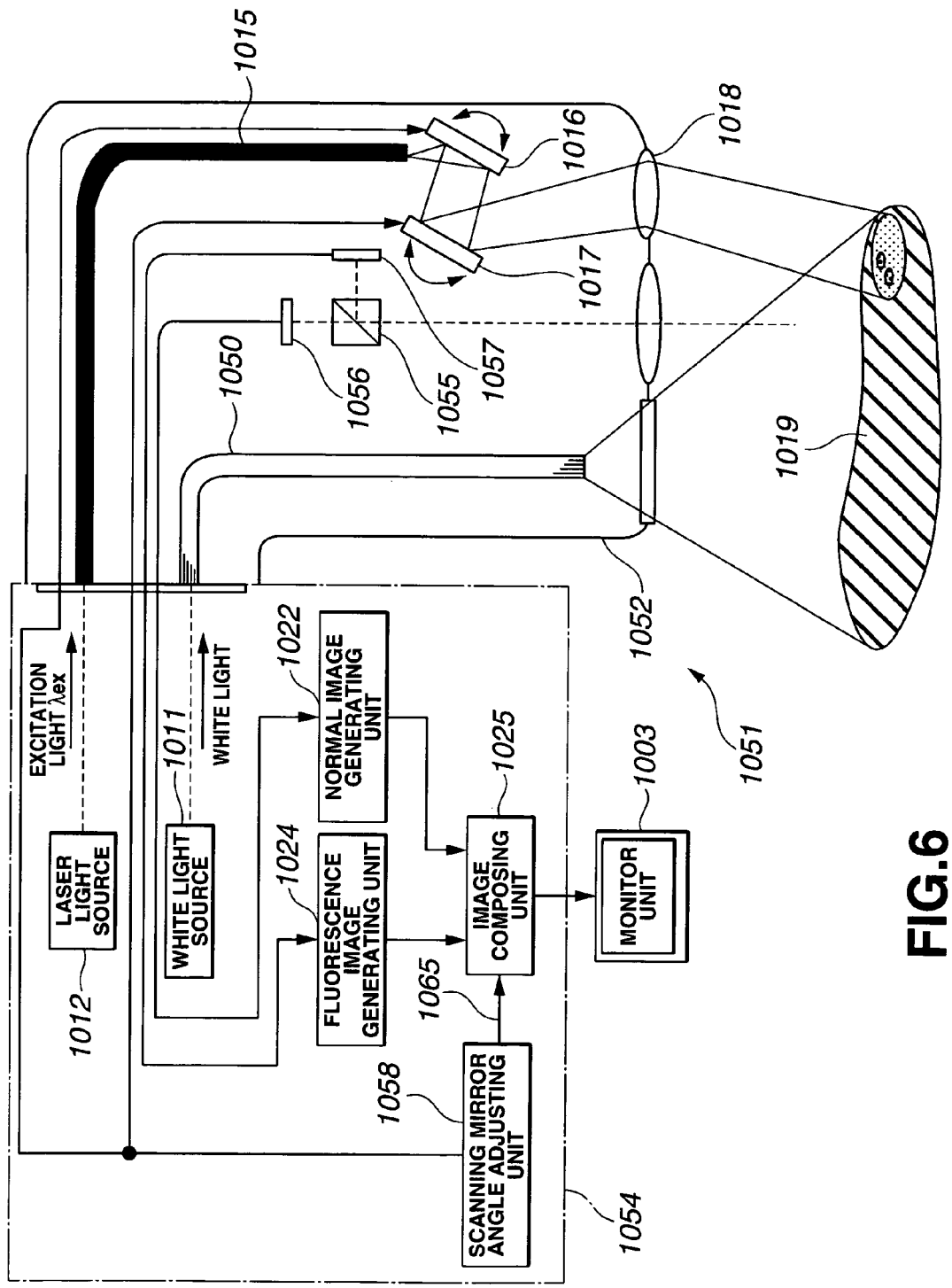
FIGS. 6 through 9 relate to an embodiment 2 according to the present invention.

As shown in FIG. 6, a fluorescence endoscope image generating device 1051 according to the present embodiment comprises: an insertion unit 1052 for being inserted into the body cavity for acquiring an image of the living body tissue therewithin; and an observation processing device 1054 for performing signal processing for captured signals of a living body tissue image acquired by the insertion unit 1052 and displaying the living body tissue image on the monitor unit 1003 as well as supplying excitation light and white light to the insertion unit 1052.

The insertion unit 1052 according to the present embodiment includes a light guide fiber bundle 1050 therewithin for transmitting white light, which is emitted from the white light source 11 of the observation processing device 1054, to the distal end thereof. On the other hand, the excitation light $\lambda$ex emitted from the laser light source 1012 of the observation processing device 1054 is introduced into the x-axis scanning mirror 1016 and the y-axis scanning mirror 1017 through the single optical fiber 1015 in the same way as with the embodiment 1. The excitation light $\lambda$ex thus introduced is two-dimensionally scanned by actions of the x-axis scanning mirror 1016 and the y-axis scanning mirror 1017, thereby casting the excitation light $\lambda$ex over a predetermined region (e.g., region of 10% or more of the normal observation region) through the condenser lens 1018.

Note that with the present embodiment, the x-axis scanning mirror 1016 and the y-axis scanning mirror 1017 are controlled by a scanning mirror angle adjusting unit 1058 included in the observation processing device 1054.

Furthermore, the insertion unit 1052 according to the present embodiment includes a half mirror 1055, a CCD 1056 for normal observation, and a CCD 1057 for fluorescence observation. With such a configuration, reflected white light is introduced into the CCD 1056 for normal observation via the half mirror 1055, thereby capturing an image of the reflected white light. On the other hand, fluorescence λem is introduced into the CCD 1057 for fluorescence observation via the half mirror 1055, thereby capturing a fluorescence image.

Then, with the observation processing device 1054, the captured signal from the CCD 1057 is subjected to signal processing in the fluorescence image generating unit 1022, thereby generating a fluorescence image of a part of the living body tissue 1019, in the same way as with the embodiment 1. Furthermore, the captured signal from the CCD 1056 is subjected to the normal image generating unit 1024, thereby generating a normal image of a part of the living body tissue 1019, in the same way as with the embodiment 1.

The image composing unit 1025 of the observation processing device 1054 generates a composite image in which a fluorescence image is superimposed on a normal image in the same way as with the embodiment 1. With the present embodiment, the image composing unit 1025 calculates the position of each fluorescence image in the image region of the normal image based upon mirror angle information 1065 received from the scanning mirror angle adjusting unit 1058 so as to compose the fluorescence image and the normal image into a single image.

The other configuration and operation are the same as with the embodiment 1.

Figure 7:
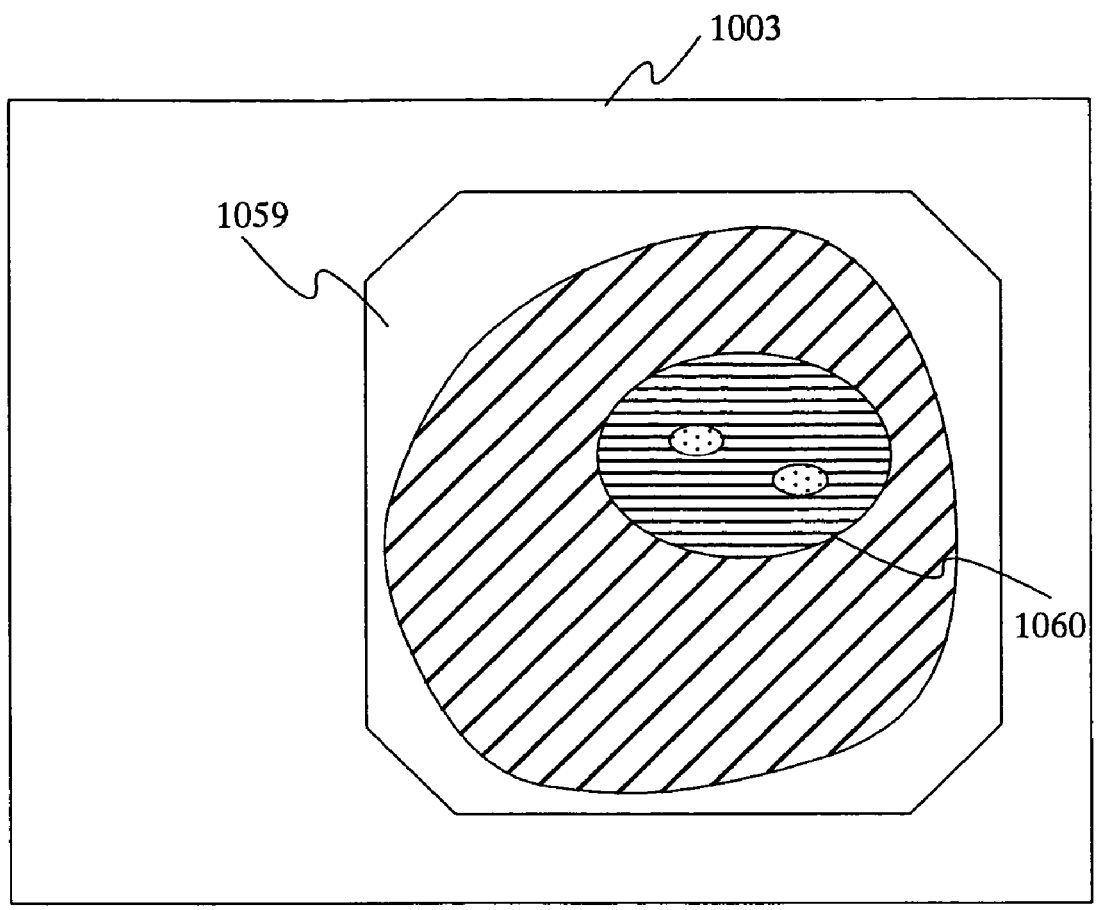

With the present embodiment, instead of casting the excitation light over the entire region of normal observation, the excitation light cast to a limited part is condensed and two-dimensionally scanned. This enables fluorescence to be efficiently excited using a laser light with a relatively low output intensity. Thus, as shown in FIG. 7, the present embodiment enables fluorescence observation with a region 1060 having a sufficient area for the user distinguishing living body tissues in an endoscope observation image 1059 displayed on the monitor unit 1003 while suppressing deterioration in the laser light source.

Figure 8:
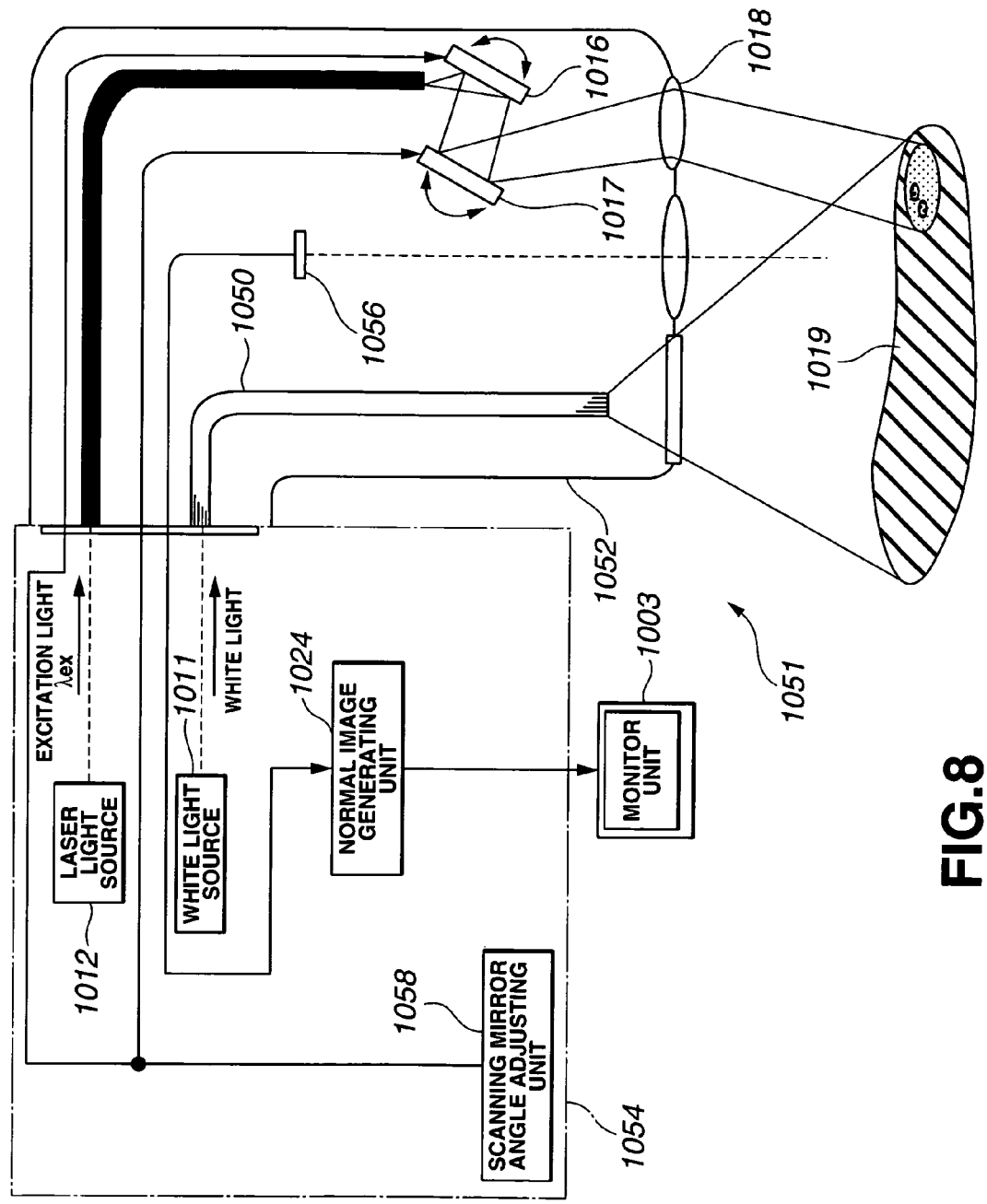
Figure 9:
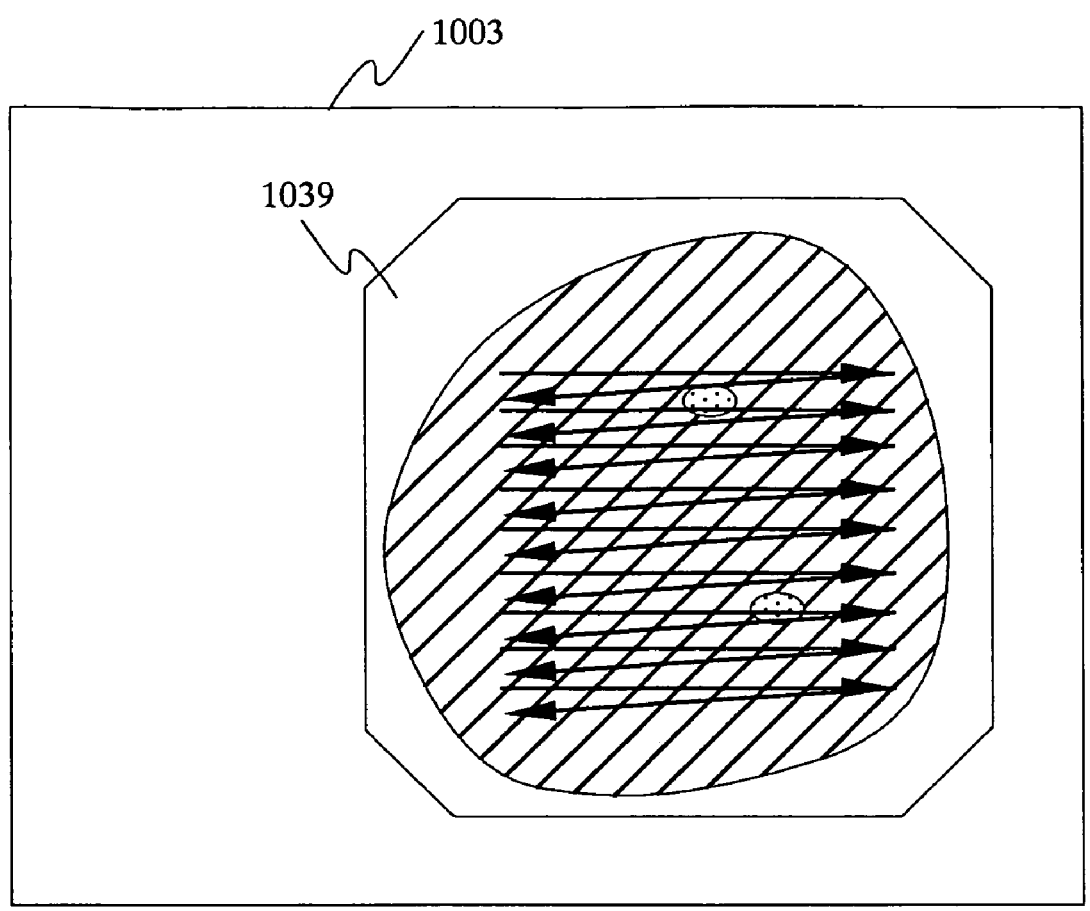

Furthermore, as shown in FIG. 8, an arrangement may be made in which a fluorescence image is captured using the CCD 1056 by two-dimensionally scanning the x-axis scanning mirror 1016 and the y-axis scanning mirror 1017 with a scanning rate matching the frame rate of the CCD 1056. Such an arrangement requires no image composing unit 1025. With such an arrangement, the normal image is updated with a video rate at the normal image generating unit 1024. On the other hand, the fluorescence image is updated with the slower of: the scanning rate of the scanning mechanism formed of the x-axis scanning mirror 1016 and the y-axis scanning mirror 1017; and the frame rate of the CCD 1056, as shown in FIG. 9.

Embodiment 3

An embodiment 3 has generally the same configuration as that of the embodiment 2. Accordingly, description will be made regarding only components that differ between these embodiments. On the other hand, the same components are denoted by the same reference numerals, and description thereof will be omitted.

Figure 10:
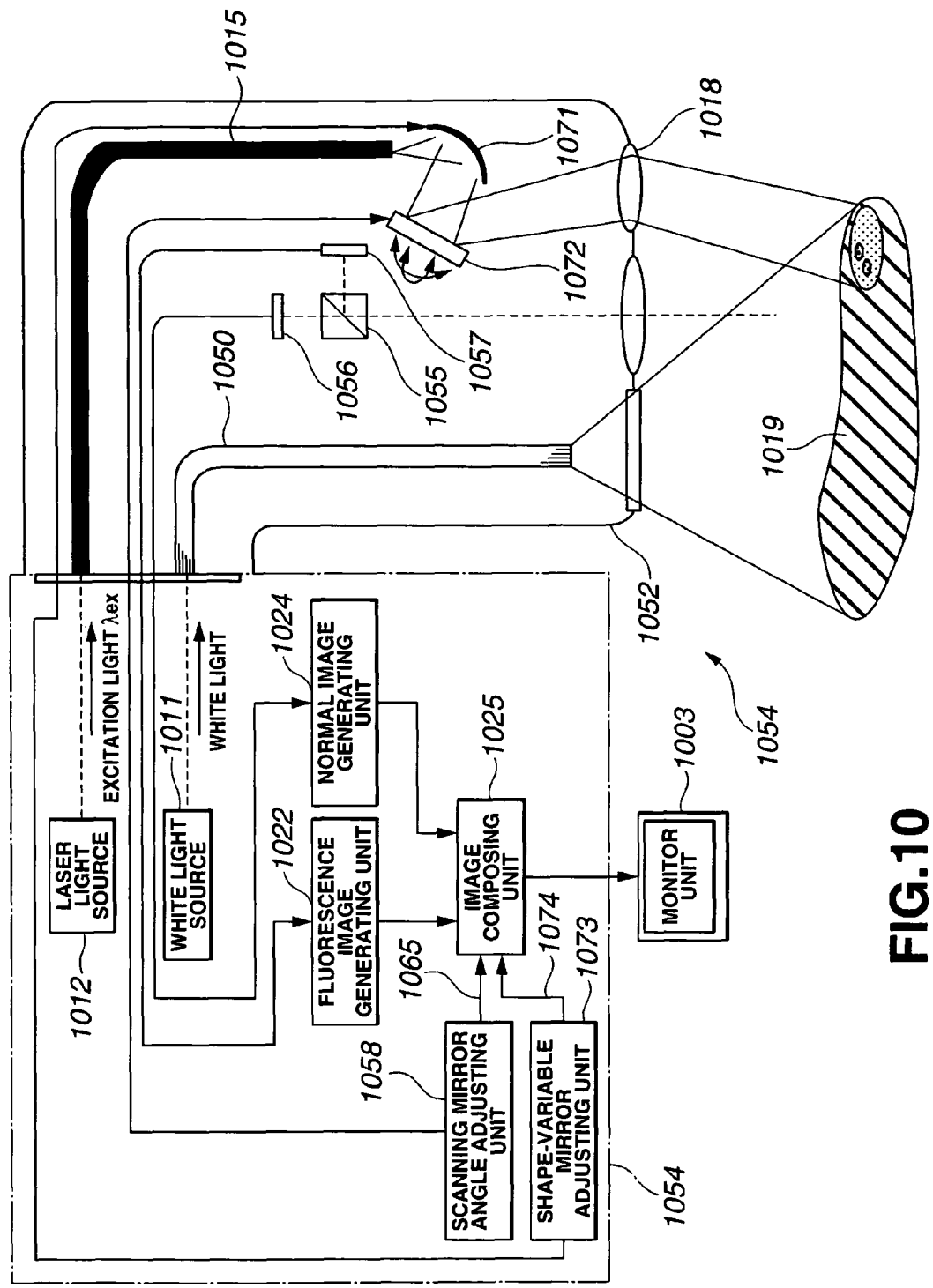
FIGS. 10 through 14 relate to an embodiment 3 according to the present invention.

As shown in FIG. 10, the scanning mechanism for two-dimensionally scanning the excitation light comprises a shape-variable mirror 1071 and an xy-axis scanning mirror 1072.

The xy-axis scanning mirror 1072 is known as a component of a micromachined scanning confocal optical microscope disclosed in Document "Micromachined scanning confocal optical microscope OPTICS LETTERS Vol. 21, No. 10, May, 1996", for example. Accordingly, description thereof will be omitted.

With the present embodiment, the shape-variable mirror 1071 is controlled by a shape-variable mirror adjusting unit 1073 of the observation processing device 1054. On the other hand, the xy-axis scanning mirror 1072 is controlled by the scanning mirror angle adjusting unit 1058 of the observation processing device 1054.

The image composing unit 1025 of the observation processing device 1054 generates a composite image in which a fluorescence image is superimposed on a normal image in the same way as with the embodiment 1. With such a configuration, the image composing unit 1025 calculates the position and region of each fluorescence image in the image region of the normal image based upon mirror angle information 1065 received from the scanning mirror angle adjusting unit 1058 and mirror shape information 1074 received from the shape-variable mirror adjusting unit 1073 so as to compose the fluorescence image and the normal image into a single image.

Figure 11:
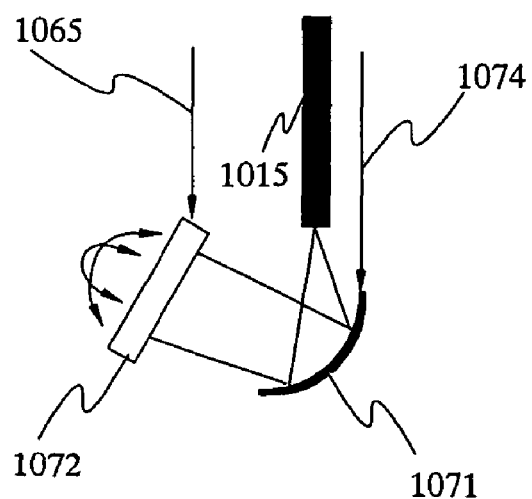
Figure 12:
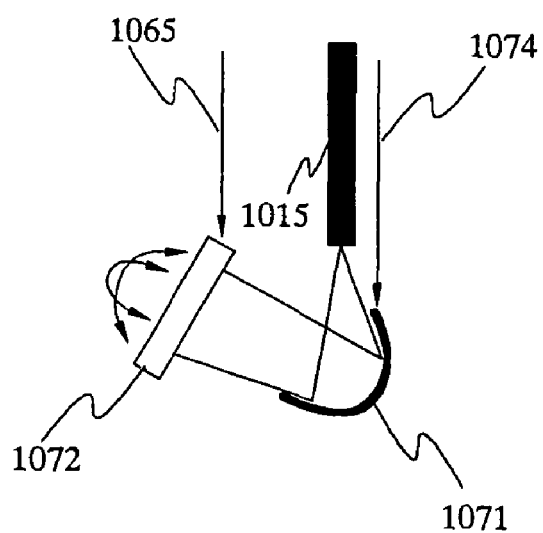
Figure 13:
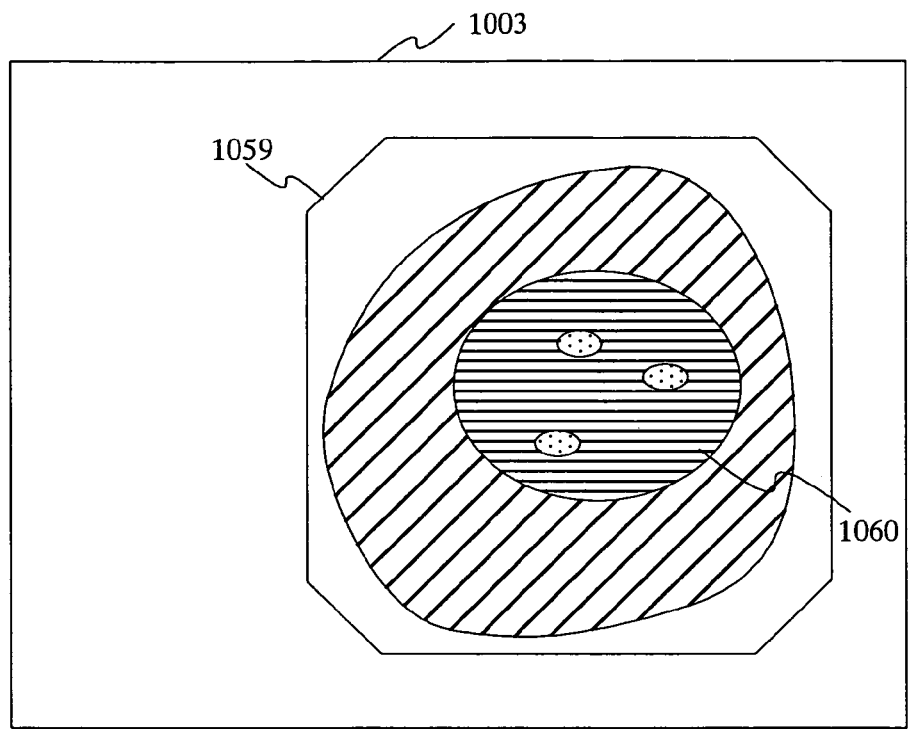
Figure 14:
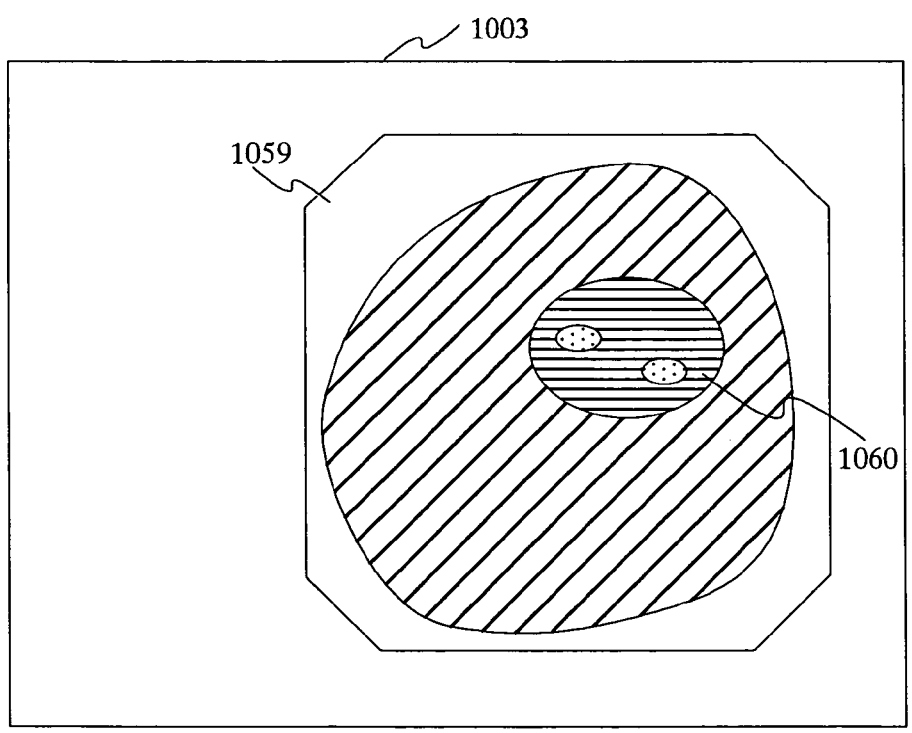

Thus, the present embodiment has advantages in addition to the advantages of the embodiment 2 as follows. That is to say, the present embodiment allows the shape of the shape-variable mirror 1071 to be varied according to the mirror-angle information 1065 received from the scanning mirror angle adjusting unit 1058 and the mirror-shape information 1074 received from the shape-variable mirror adjusting unit 1073. For example, the shape of the shape-variable mirror 1071 can be varied from the state shown in FIG. 11 to the state shown in FIG. 12. Such a configuration allows the user to vary the region 1060 of the fluorescence image displayed on the monitor unit 1003. For example, the user can vary the region 1060 of the fluorescence image from the state shown in FIG. 13 to the state shown in FIG. 14. Furthermore, the present embodiment enables variation of the illumination intensity of the excitation light per unit area, thereby allowing the user to select the optimum illumination intensity.

Embodiment 4

Figure 15:
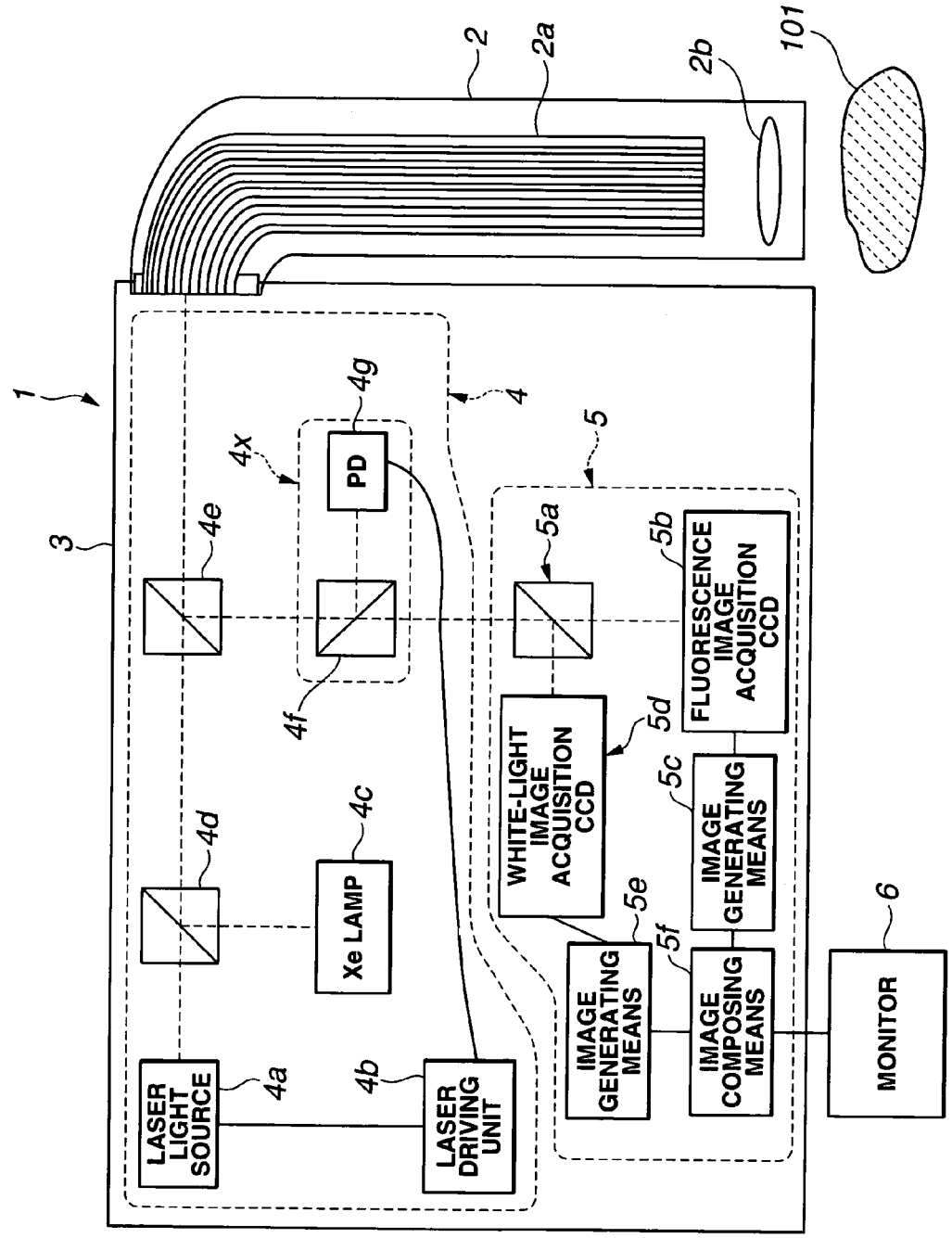

An image generating device 1 according to the present embodiment comprises: an insertion unit 2 having a size, shape, and flexibility which allows at least a part thereof to be inserted into the body cavity; a device main unit 3 having a configuration which allows detachable mounting thereof to the insertion unit 2 and having a function of generating an image based upon light cast from the insertion unit 2; and a monitor 6 for displaying an image based on the image signal output from the device main unit 3, as shown in FIG. 15.

Furthermore, the device main unit 3 comprises: a light source device 4 having a function of emitting two kinds of light, i.e., white light and excitation light for exciting fluorescence in each organ within the living body administered with a fluorescent material beforehand for fluorescence observation; and a processor 5 having functions such as a function of generating an image based upon fluorescence emitted from a subject 101 due to the excitation light cast from the light source device 4 and the reflected white light which is white light reflected by the subject 101.

The insertion unit 2 comprises an light introducing portion 2a provided so as to be inserted into the inside of the insertion unit 2; and an object optical system 2b provided to the distal end of the insertion unit 2.

The light introducing portion 2a is formed of quartz fibers or the like, and has a function of introducing the excitation light cast from the light source device 4 to the subject 101, i.e., each organ within the living body, as well as a function of serving as a second light introducing portion for introducing fluorescence emitted from the subject 101 due to the excitation light cast from the light source device 4, to the device main unit 3.

Furthermore, the light introducing portion 2a has a function of introducing white light cast from the light source device 4 to the subject 101, i.e., each organ within the living body, as well as a function of introducing the reflected white light, which is white light reflected by the subject 101, to the device main unit 3. Furthermore, the light introducing portion 2a introduces the reflected excitation light, which is the excitation light reflected by the subject 101, to the device main unit 3.

The object optical system 2b has a function of casting the white light and the excitation light output from the light introducing portion 2a onto the subject 101. Furthermore, the object optical system 2b has a function of condensing the fluorescence emitted from the subject 101, the reflected white light which is white light emitted from the light source device 4 reflected by the subject 101, and the reflected excitation light, on the light introducing portion 2a.

The light source device 4 comprises a laser light source 4a, a laser driving unit 4b, a xenon (Xe) lamp 4c for emitting white light, a mirror 4d, a mirror 4e, and a luminous intensity detecting unit 4x. Furthermore, the luminous intensity detecting unit 4x comprises a mirror 4f and a photodiode (which will be referred to as "PD" hereafter) 4g.

The laser light source 4a serving as a light source has a function of emitting excitation light which is laser light in a wavelength range including the excitation wavelength for the fluorescent material with which each organ within the living body is administered for fluorescence observation, thereby exciting fluorescence in each organ within the living body administered with the fluorescent material.

The laser driving unit 4b performs driving control of the laser light source 4a based upon a predetermined signal such as a luminous intensity signal or the like output from the luminous intensity detecting unit 4x.

Note that description will be made later regarding the luminous intensity signal output from the luminous intensity detecting unit 4x and the driving control performed based upon the luminous intensity signal.

The xenon lamp 4c which is a white light source outputs white light in a wavelength range including visible light. Note that the excitation light output from the laser light source 4a and the white light output from the xenon lamp 4c are introduced to the same optical path by the mirror 4d serving as a light composing unit. The light composed of two kinds of light, i.e., the excitation light and the white light, passes through the mirror 4e provided on the aforementioned optical path, and is input to the insertion unit 2.

As described above, the mirror 4e allows the light composed of the two kinds of light, i.e., the excitation light and the white light to pass therethrough, as well as reflecting fluorescence, the reflected white light, and the reflected excitation light, which have been output from the insertion unit 2, so as to be output to the luminous intensity detecting unit 4x.

The mirror 4f serving as a light separator has a function of allowing the fluorescence and the reflected white light, of the components, the fluorescence, the reflected white light, and the reflected excitation light, to pass therethrough, as well as having a function of reflecting the reflected excitation light. These functions allow the light output from the mirror 4e to be separated into the fluorescence and the reflected excitation light. Then, the fluorescence and the reflected white light which have passed through the mirror 4f are output to the processor 5. On the other hand, the reflected excitation light reflected by the mirror 4f is output to the PD 4g.

The PD 4g, which is a third photo-detecting unit, detects the reflected excitation light separated by the mirror 4f, and outputs the luminous intensity signal to the laser driving unit 4b with a voltage level corresponding to the light amount of the reflected excitation light by actions of photoelectric conversion.

The processor 5 comprises a mirror 5a, a fluorescence image acquisition charge coupled device (which will be referred to as "CCD" hereafter) 5b, a white light image acquisition CCD 5d, and an image generating block unit 5x. Furthermore, the image generating block unit 5x comprises image generating units 5c, 5e, and 5f.

The mirror 5a has a function of allowing the fluorescence to pass therethrough, as well as having a function of reflecting the reflected white light. These functions enable the light output from the luminous intensity detecting unit 4x to be separated into the fluorescence and the reflected white light. Then, the fluorescence which has passed through the mirror 5a is output to the fluorescence image acquisition CCD 5b. On the other hand, the reflected white light reflected by the mirror 5a is output to the white light image acquisition CCD 5d.

The fluorescence image acquisition CCD 5b serving as a first photo-detecting unit detects the fluorescence output from the mirror 5a, converts the detected fluorescence into a fluorescence image signal, and outputs the fluorescence image signal to the image generating unit 5c.

The image generating unit 5c serving as a fluorescence image generating unit generates a fluorescence image which is an image of the subject 101 due to fluorescence based upon the fluorescence image signal output from the fluorescence image acquisition CCD 5b, and outputs the fluorescence image thus generated, to the image composing unit 5f.

The white light image acquisition CCD 5d serving as a second photo-detecting unit detects the reflected white light output from the mirror 5a, converts the reflected white light thus detected into a white light image signal, and outputs the white light image signal to the image generating unit 5e.

The image generating unit 5e serving as a white light image generating unit generates a white light image which is an image of the subject 101 due to reflected white light based upon the white light image signal output from the white light image acquisition CCD 5d, and outputs the white light image thus generated, to the image composing unit 5f.

The image composing unit 5f composes the fluorescence image output from the image generating unit 5c and the white light image output from the image generating unit 5e into a single image at output timings synchronous with each other, and outputs the composite image to the monitor 6.

The monitor 6 which is a display unit has a function of displaying a single image alone selected from the fluorescence image output from the image generating unit 5c and the white light image output from the image generating unit 5e. Furthermore, the monitor 6 has a function of displaying both the aforementioned images at the same time. Thus, the monitor 6 displays the image output from the image composing unit 5f.

Next, description will be made regarding the operation of the image generating unit 1 according to the present embodiment for observation of the organ within the living body, with reference to FIGS. 15 through 20.

Let us say that an operator observes the living body using the image generating device 1 according to the present embodiment. In this case, first, the operator connects the insertion unit 2 to the device main unit 3. Following insertion of the insertion unit 2 into the body cavity, the power supply is turned on for the laser light source 4a, the xenon lamp 4c, and so forth, whereby the laser light source 4a and the xenon lamp 4c emit light. Then, the operator inserts the insertion unit 2 into the vicinity of the organ within the living body which are to be observed and which have been administered with a fluorescent material for fluorescence observation so that the image of the subject 101 is displayed on the monitor 6.

In this case, the situation in which the distal end of the insertion unit 2 comes in contact with the subject 101, for example, may lead to a problem that the excitation light of an excessive luminous intensity is cast onto the subject 101. The present embodiment addresses this problem as follows. That is to say, the PD 4g which is a component of the luminous intensity detecting unit 4x detects the reflected excitation light output from the insertion unit 2, through the mirrors 4e and 4f.

Figure 16:
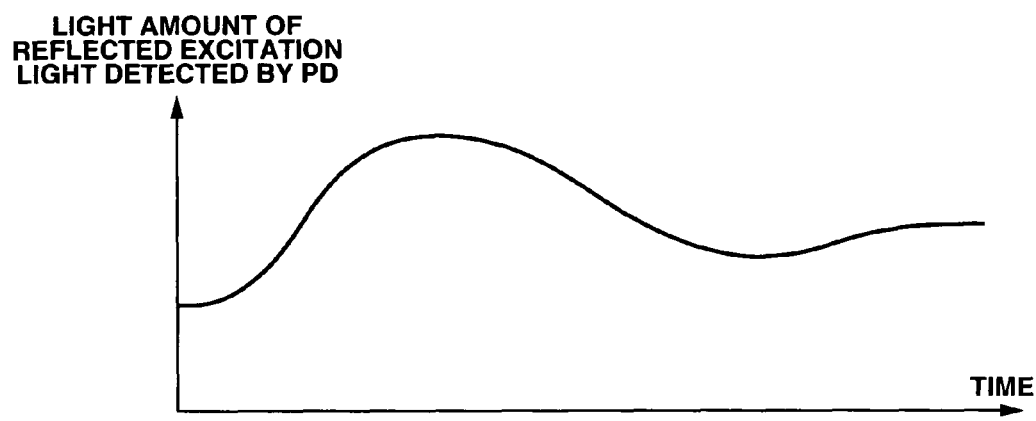
Figure 17:
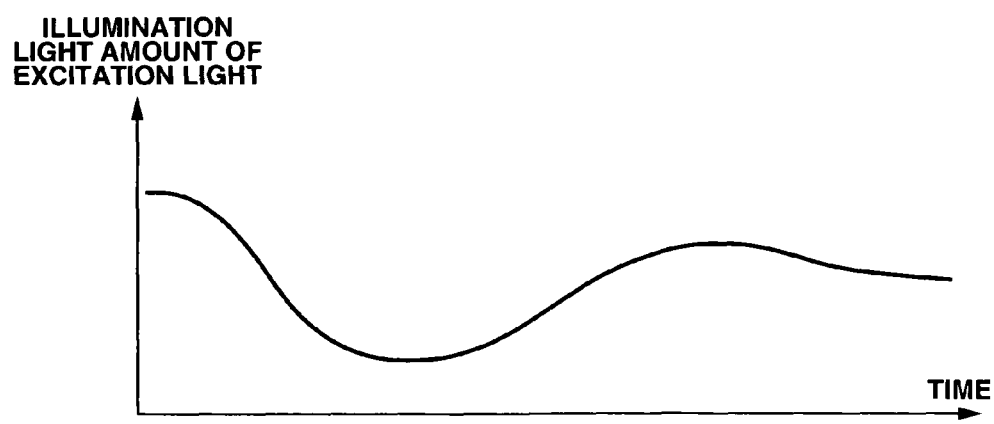

Then, the PD 4g outputs the luminous intensity signal to the laser driving unit 4b with a voltage level corresponding to the light amount of the reflected excitation light thus detected by actions of photoelectric conversion as shown in FIG. 16. The laser driving unit 4b which is an illumination light adjusting unit serving as a light source output adjusting unit varies the driving current output to the laser light source 4a based upon the aforementioned luminous intensity signal, thereby adjusting the luminous intensity output from the laser light source 4a as shown in FIG. 17.

Figure 18:
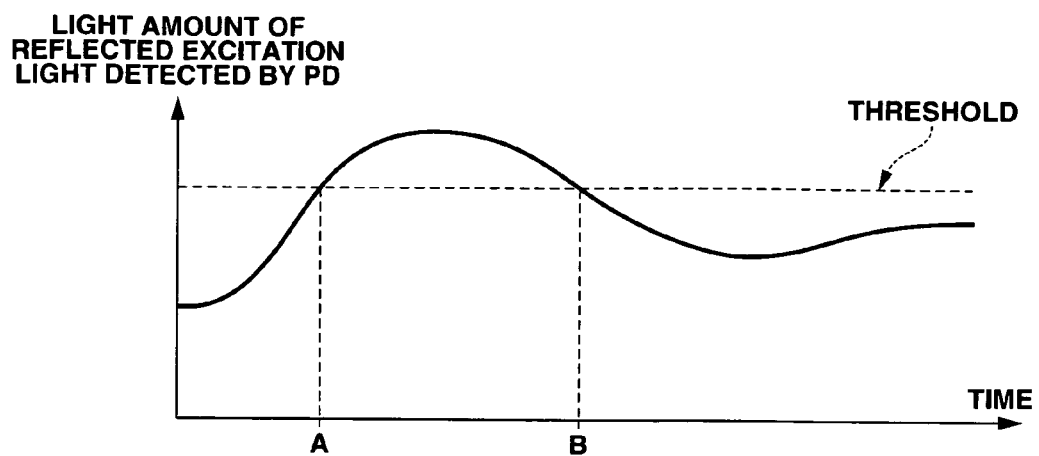

Note that the adjusting method for the luminous intensity of the excitation light according to the present embodiment is not restricted to the arrangement described above with reference to FIGS. 16 and 17. Also, an arrangement may be made in which the luminous intensity is adjusted based upon the comparison result between the light amount of the reflected excitation light detected by the PD 4g and a threshold set beforehand, as shown in FIGS. 18 and 19, for example.

With such an arrangement, the PD 4g outputs the luminous intensity signal to the laser driving unit 4b only for the duration from of a time point A to a time point B for which the light amount of the reflected excitation light exceeds the threshold. Then, the laser driving unit 4b varies the driving current output to the laser light source 4a based upon the aforementioned luminous intensity signal, thereby adjusting the luminous intensity only for the duration between the time points A and B. Thus, the laser driving unit 4b varies the luminous intensity of the excitation light cast from the laser light source 4a as shown in FIG. 19.

Figure 19:
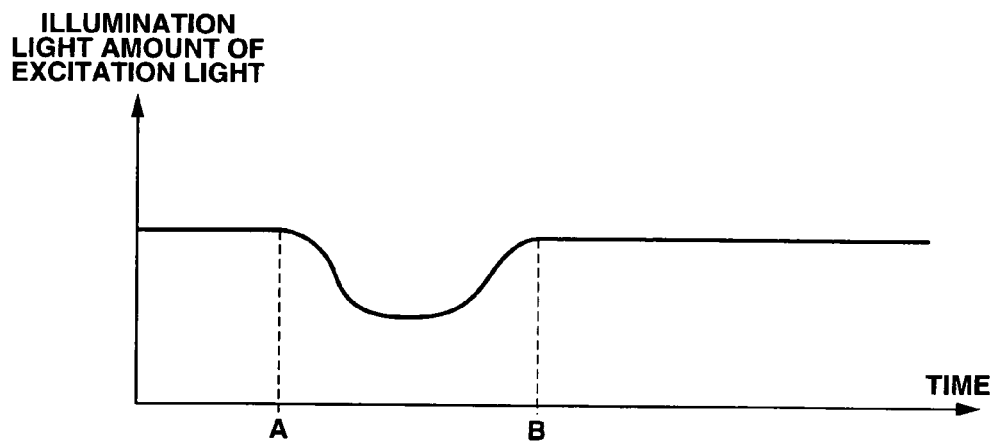
Figure 20:
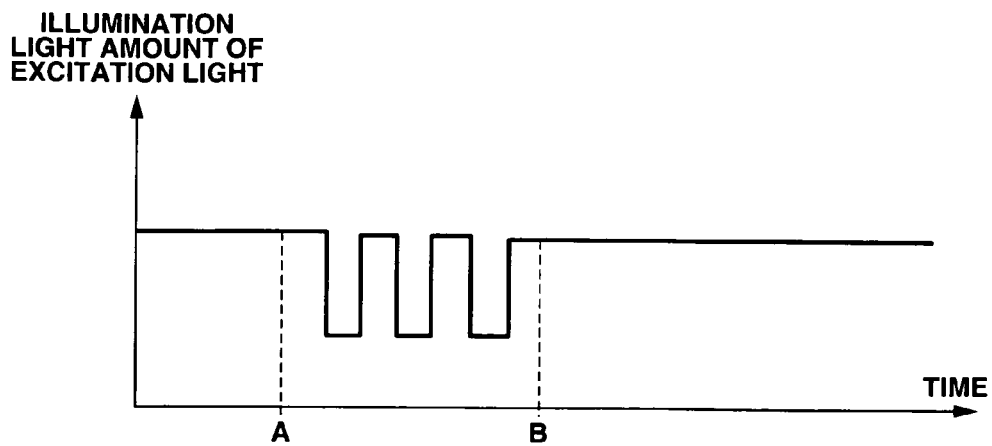

Note that the adjustment of the illumination light for the duration of the time point A to the time point B is not restricted to the arrangement shown in FIG. 19. Also, an arrangement may be made in which the luminous intensity of the excitation light is adjusted in the form of pulse output as shown in FIG. 20, for example.

Modification 1 of the Embodiment 4

Figure 21:
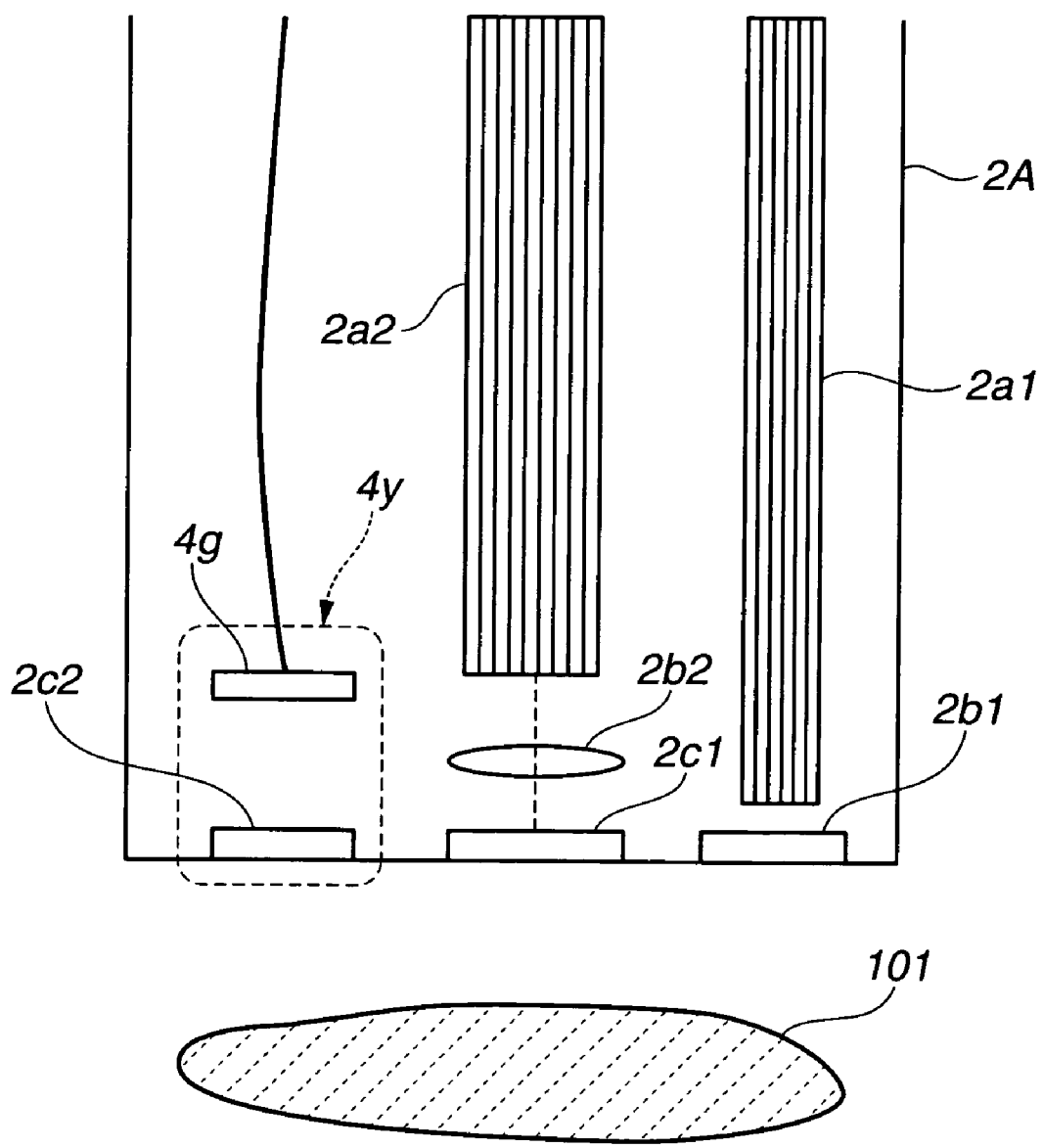
Figure 22:
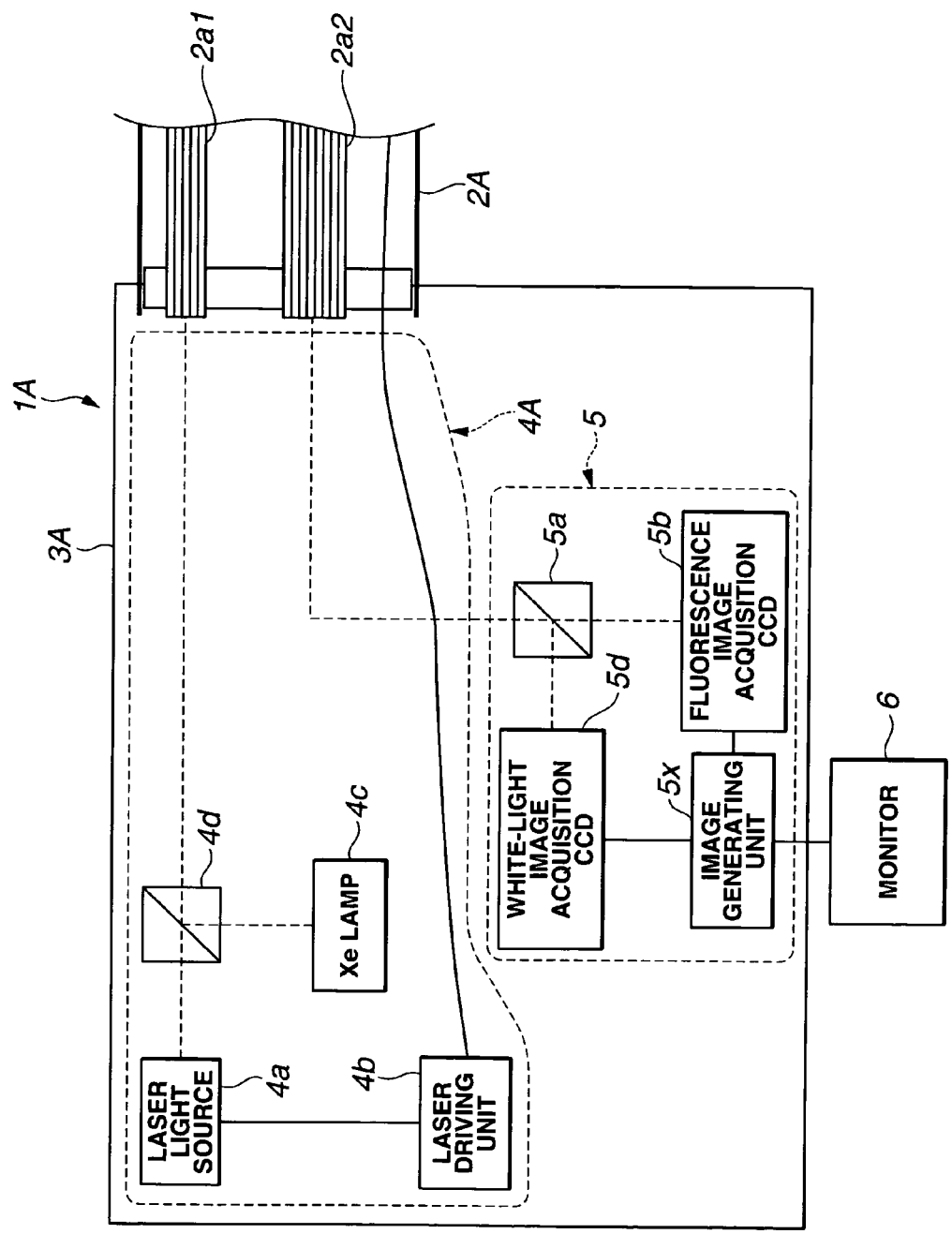

Also, as a modification 1 of the present embodiment, an image generating device 1A has a configuration comprising an insertion unit 2A as shown in FIG. 21, a light source device 4A as shown in FIG. 22, a device main unit 3A including the processor 5 having the same configuration as described above, and the monitor 6 having the same configuration as described above.

The insertion unit 2A includes a light introducing portions 2a1 and 2a2 inserted into the inside thereof. Furthermore, the insertion unit 2A includes object optical systems 2b1 and 2b2, an excitation-light cut-off filter 2c1, and a luminous intensity detecting unit 4y, at the distal end thereof. Furthermore, the luminous intensity detecting unit 4y comprises an excitation-light transmission filter 2c2, and a PD 4g.

The light introducing portion 2a1 which is a first light introducing portion is formed of quartz fibers or the like, and has a function of introducing the excitation light and the white light output from the light source device 4A to the subject 101, i.e., the organ within the living body. On the other hand, the light introducing portion 2a2 which is a second light introducing portion is formed of quartz fibers or the like, and has a function of introducing fluorescence, which has been emitted from the subject 101 due to the excitation light output from the light source device 4A, to the device main unit 3A. Furthermore, the light introducing portion 2a2 introduces the reflected white light, which is white light emitted from the light source device 4A and reflected by the subject 101, to the device main unit 3A.

The object optical system 2b1 has a function of casting the excitation light and the white light, which have been output from the light introducing portion 2a1, onto the subject 101.

The excitation cut-off filter 2c1 has a function of shielding the reflected white light as well as having a function of allowing the fluorescence emitted from the subject 101 and the reflected white light to pass therethrough. With the present embodiment, the fluorescence and the reflected white light which have passed therethrough are output to the object optical system 2b2.

The object optical system 2b2 condenses the fluorescence and the reflected white light, which have been output from the excitation-light cut-off filter 2c1, on the light introducing portion 2a2.

The excitation light transmission filter 2c2 serving as a light separator has a function of shielding the fluorescence and the reflected white light, which are components of the light emitted from or reflected by the subject 101, i.e., the light composed of the fluorescence emitted from the subject 101, the reflected white light, and the reflected excitation light, as well as having a function of allowing the reflected excitation light to pass therethrough. These functions enable separation of the reflected excitation light from the fluorescence. The reflected excitation light, which has passed through the excitation light transmission filter 2c2, is output to the PD 4g.

Note that the PD 4g performs the same operation as described above, and accordingly, description thereof will be omitted in the present modification.

The light source device 4A comprises the laser light source 4a, the laser driving unit 4b, the xenon lamp 4c for emitting white light, and the mirror 4d. That is to say, the light source device 4A has generally the same configuration as that of the light source device 4 described above, except that it does not include the mirror 4e and the luminous intensity detecting unit 4x.

Note that each component thereof performs generally the same operation as described above, and accordingly, description thereof will be omitted in the present modification.

Modification 2 of Embodiment 4

Figure 23:
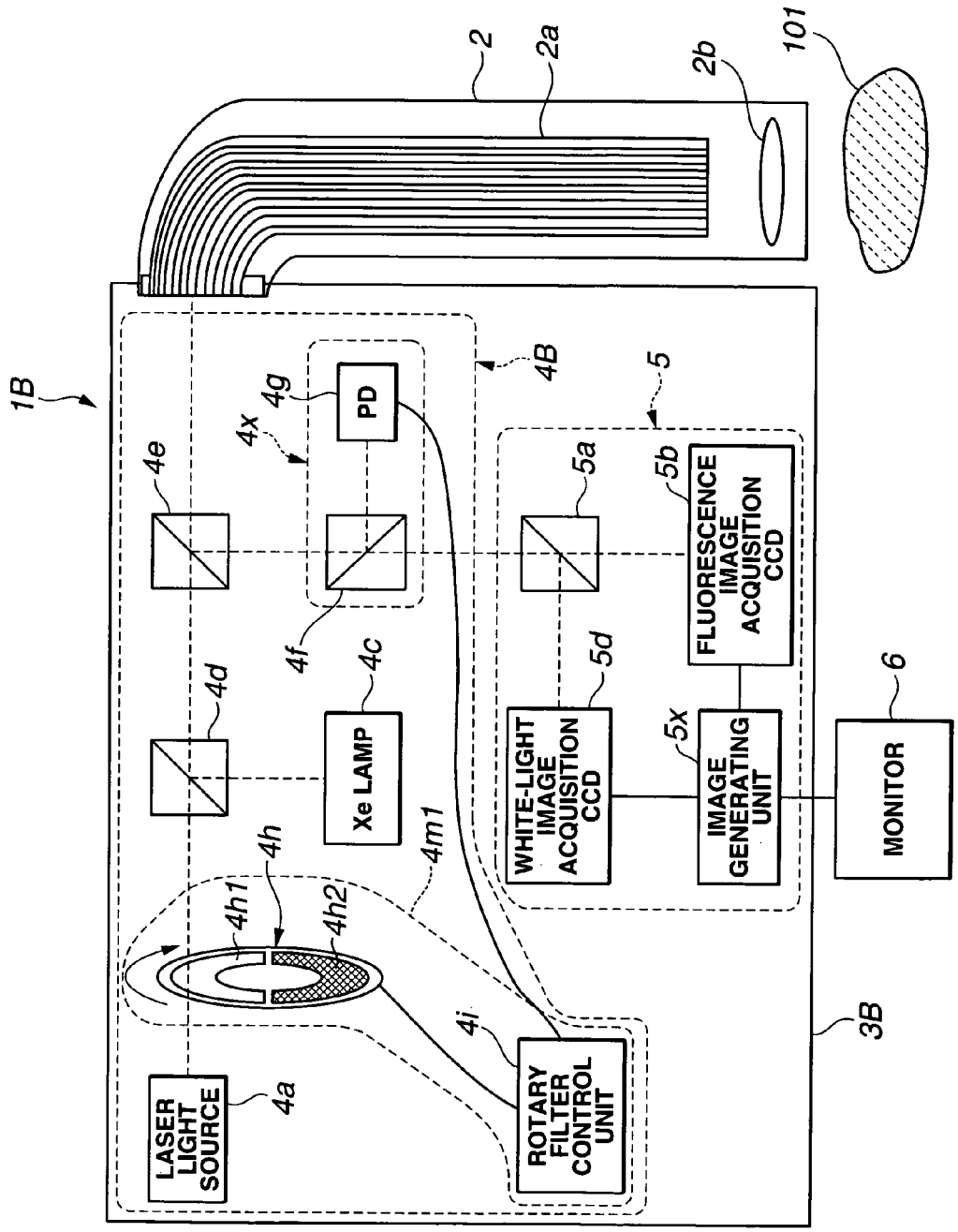

The illumination light adjusting unit according to the present embodiment is not restricted to the arrangement in which the laser driving unit 4b controls the driving current input to the laser light source 4a. Also, a modification 2 may be made according to the present embodiment as shown in FIG. 23, for example. That is to say, an image generating device 1B may comprise the insertion unit 2 having the same configuration as described above, a light source device 4B, a device main unit 3B including the processor 5 having the same configuration as described above, and the monitor 6 having the same configuration as described above.

The light source device 4B comprises the laser light source 4a, the xenon lamp 4c for emitting white light, the mirrors 4d and 4e, the luminous intensity detecting unit 4x, and an illumination light adjusting unit 4m1.

Furthermore, the illumination light adjusting unit 4m1 comprises a rotary filter 4h and a rotary filter control unit 4i. That is to say, the light source device 4B includes the rotary filter 4h and the rotary filter control unit 4i, instead of the laser driving unit 4b included in the light source device 4 described above.

Note that description will be omitted regarding the components having the same configuration and the same function as described above.

The rotary filter 4h which is a variable-transmissivity unit includes a transmission filter 4h1 for allowing the excitation light output from the laser light source 4a to pass therethrough, and a shielding filter 4h2 for shielding the excitation light output from the laser light source 4a, provided around the circumference thereof with generally the same area. The rotary filter 4h is provided on the optical path for the laser light source 4a. With such a configuration, the rotary filter 4h is driven and rotated with a predetermined revolution when driven by the rotary filter control unit 4i, thereby inserting the transmission filter 4h1 and the shielding filter 4h2 on the optical path for the laser light source 4a in alternating order.

The rotary filter control unit 4i performs driving control of the rotary filter 4h based upon the luminous intensity signal output from the luminous intensity detecting unit 4x.

Let us say that the excitation light of excessive luminous intensity is cast onto the subject 101 in fluorescence observation using the image generating device 1B according to the present modification, for example. In this case, the PD 4g detects the reflected excitation light output from the insertion unit 2 through the mirrors 4e and 4f. Then, the PD 4g outputs the luminous intensity signal with a voltage level as shown in FIG. 16 corresponding to the light amount of the reflected excitation light thus detected by actions of photoelectric conversion, to the rotary filter control unit 4i. The rotary filter control unit 4i changes the revolution of the rotary filter 4h based upon the aforementioned luminous intensity signal. This enables variation of the transmissivity of the rotary filter 4h with respect to the excitation light continuously, thereby allowing adjustment of the illumination light so that the excitation light is cast onto the subject 101 with generally the same light amount as shown in FIG. 17.

Note that the control mechanism of the rotary filter control unit 4i for controlling the excitation light output from the laser light source 4a is not restricted to the aforementioned arrangement. Also, an arrangement may be made as described below.

That is to say, in a case that the PD 4g has detected the reflected excitation light of a light amount greater than a predetermined threshold value over the period from time point A to time point B, and accordingly, the PD 4g has output a luminous intensity signal to the rotary filter control unit 4i with a voltage level corresponding to the reflected excitation light, for example, the rotary filter control unit 4i controls on/off of the rotation of the rotary filter 4h, thereby allowing variation of the transmissivity of the rotary filter 4h with respect to the excitation light in an on/off manner. This enables adjustment of the illumination light so that the excitation light is cast with generally the same light amount as shown in FIG. 20.

Modification 3 of Embodiment 4

Also, modification 3 may be made according to the present embodiment, including multiple illumination light adjusting units each of which is a variable-transmissivity unit as shown in FIG. 24. That is to say, an image generating unit 1C may comprise the insertion unit 2 having the same configuration as described above, a light source device 4C, a device main unit 3C including the processor 5 having the same configuration as described above, and the monitor 6 having the same configuration as described above.

The light source device 4C includes the laser light source 4a, the xenon lamp 4c for emitting white light, the mirrors 4d and 4e, the luminous intensity detecting unit 4x, and an illumination light adjusting unit 4m2. Furthermore, the illumination light adjusting unit 4m2 comprises the rotary filter 4h, the rotary filter control unit 4i, and a rotary filter 4j. That is to say, the light source device 4C has generally the same configuration as that of the light source device 4B described above, except for further including the rotary filter 4j.

The rotary filter 4j which is an illumination light adjusting unit serving as a variable-transmissivity unit includes a transmission filter 4j1 for allowing the excitation light output from the laser light source 4a to pass therethrough, and a shielding filter 4j2 for shielding the excitation light output from the laser light source 4a, provided around the circumference thereof with an area ratio of approximately 1:2. The rotary filter 4j is provided on the optical path for the laser light source 4a. With such a configuration, the rotary filter 4j is driven under the control of the rotary filter control unit 4i, thereby inserting the transmission filter 4j1 and the shielding filter 4j2 into the optical path of the illumination light emitted from the laser light source 4a in alternating order. Note that the rotary filter 4j is rotated with a predetermined revolution which is generally the same as that of the rotary filter 4h.

The rotary filter control unit 4i controls driving of the rotary filters 4h and 4j based upon the luminous intensity signal output from the luminous intensity detecting unit 4x.

The image generating device 1C according to the present modification can operate in a mode as described below. In this mode, the image generating device 1C is in the state as shown in FIG. 24. That is to say, both the rotary filters 4h and 4j are not rotated, i.e., are kept stationary with the transmission filters 4h1 and 4j1 inserted into the optical path for the laser light source 4a. Let us say that the excitation light of excessive luminous intensity is cast onto the subject 101 at the time point C, as shown in FIGS. 25 and 26. In this case, the PD 4g detects the reflected excitation light output from the insertion unit 2 through the mirrors 4e and 4f. Then, the PD 4g outputs a luminous intensity signal to the rotary filter control unit 4i with a voltage level corresponding to the light amount of the reflected excitation light thus detected by actions of photoelectric conversion. The rotary filter control unit 4$i$ rotates the rotary filter 4$h$ with a predetermined revolution based upon the aforementioned luminous intensity signal. This allows variation of the transmissivity with respect to the excitation light continuously as shown in FIG. 25, for example, thereby enabling adjustment of the period in which excitation light from the laser light source 4$a$ is cast onto the subject 101.

Furthermore, the image generating device 1C according to the present modification can operate in another mode as described below. In this mode, the rotary filter 4$h$ is rotated with the transmission filter 4$j$1 thereof inserted into the optical path for the laser light source 4$a$. Let us say that the excitation light of further excessive luminous intensity is cast onto the subject 101 at the time point D, for example. In this case, the PD 4$g$ detects the reflected excitation light output from the insertion unit 2 through the mirrors 4$e$ and 4$f$. Then, the PD 4$g$ outputs a luminous intensity signal to the rotary filter control unit 4$i$ with a voltage level corresponding to the light amount of the reflected excitation light thus detected by actions of photoelectric conversion. The rotary filter control unit 4$i$ stops rotation of the rotary filter 4$h$, and keeps the rotary filter 4$h$ stationary with the transmission filter 4$h$1 thereof inserted into the optical path for the laser light source 4$a$, as well as rotating the rotary filter 4$j$ with a predetermined revolution. This allows variation of the transmissivity with respect to the excitation light continuously as shown in FIG. 26, for example, thereby enabling adjustment of the period in which excitation light from the laser light source 4$a$ is cast onto the subject 101.

Modification 4 of Embodiment 4

Figure 27:
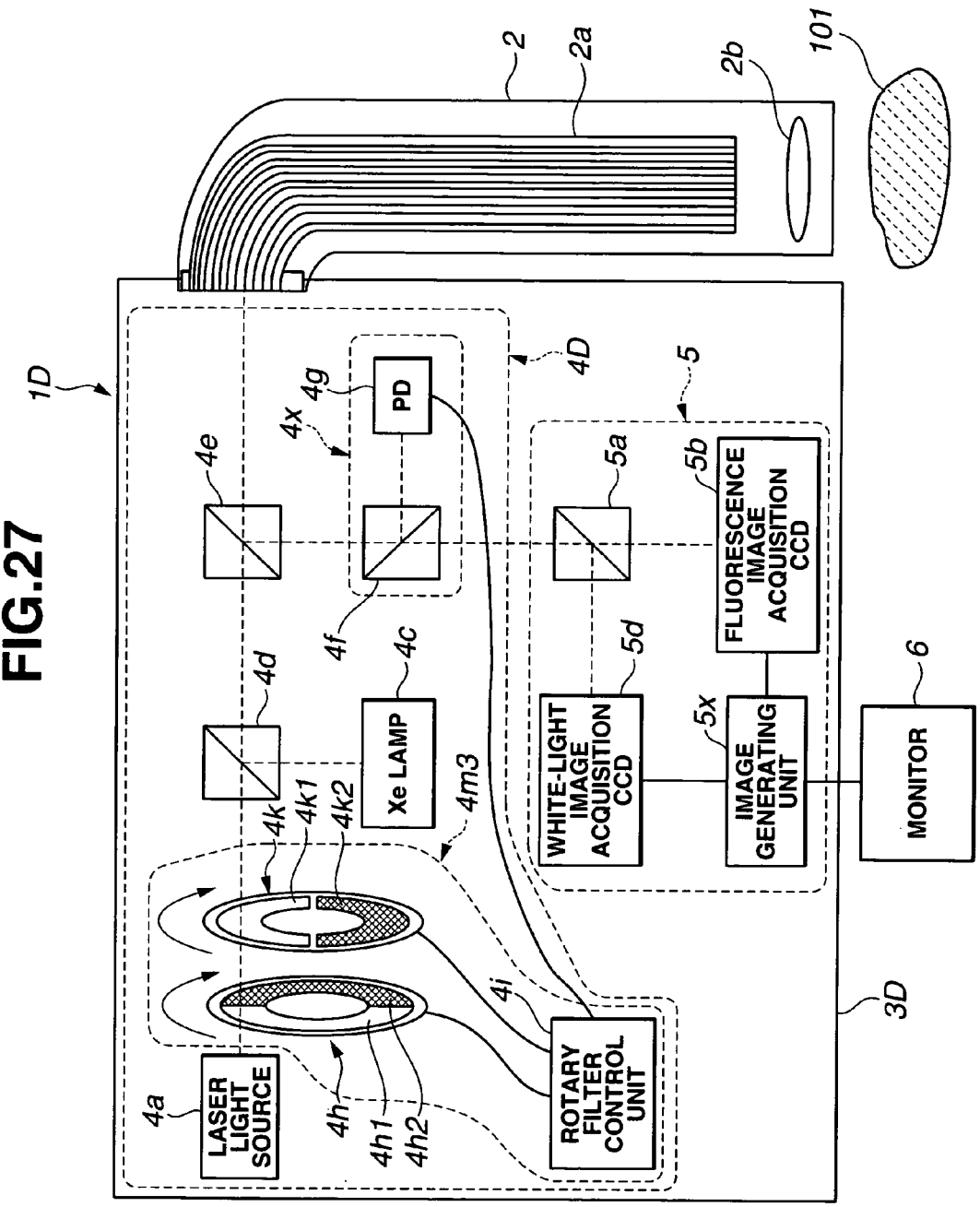

Also, a modification 4 may be made according to the present embodiment, including the multiple illumination light adjusting units each of which is a variable-transmissivity unit having generally the same structure as shown in FIG. 27. That is to say, an image generating device 1D may comprise the insertion unit 2 having the same configuration as described above, a light source device 4D, a device main unit 3D including the processor 5 having the same configuration as described above, and the monitor 6 having the same configuration as described above.

The light source device 4D includes the laser light source 4$a$, the xenon lamp 4$c$ for emitting white light, the mirrors 4$d$ and 4$e$, the luminous intensity detecting unit 4$x$, and an illumination light adjusting unit 4$m$3. Furthermore, the illumination light adjusting unit 4$m$3 comprises the rotary filter 4$h$, the rotary filter control unit 4$i$, and a rotary filter 4$k$. That is to say, the light source device 4D has generally the same configuration as that of the light source device 4B described above, except for further including the rotary filter 4$k$.

The rotary filter 4$k$ which is an illumination light adjusting unit serving as a variable-transmissivity unit comprises a transmission filter 4$k$1 for allowing the excitation light output from the laser light source 4$a$ to pass therethrough, and a shielding filter 4$k$2 for shielding the excitation light output from the laser light source 4$a$, provided around the circumference thereof with generally the same area. That is to say, the rotary filter 4$k$ has generally the same structure as that of the rotary filter 4$h$ described above. The rotary filter 4$k$ is provided on the optical path for the laser light source 4$a$. With such a configuration, the rotary filter 4$k$ is driven by the rotary filter control unit 4$i$, thereby inserting the transmission filter 4$k$1 and the shielding filter 4$k$2 into the illumination optical path for the laser light source 4$a$ in alternating order and generally consecutively. Furthermore, the rotary filter 4$k$ is rotated with a predetermined revolution which is generally the same as that of the rotary filter 4$h$, and with a phase different from that of the rotary filter 4$h$.

Figure 28:
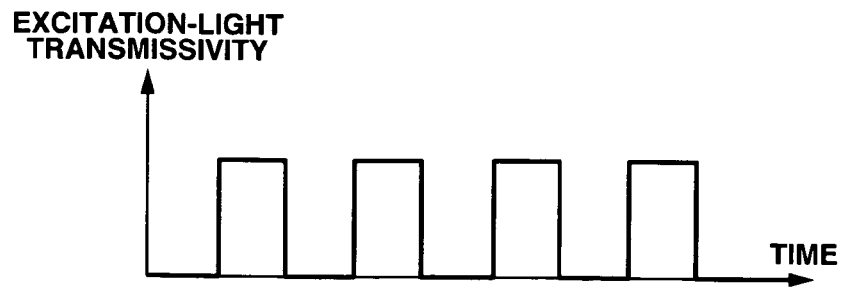

The image generating device 1D according to the present modification can operate in a mode as described below. Let us say that the excitation light of excessive luminous intensity is cast onto the subject 101, for example. In this case, the PD 4$g$ detects the reflected excitation light output from the insertion unit 2 through the mirrors 4$e$ and 4$f$. Then, the PD 4$g$ outputs a luminous intensity signal to the rotary filter control unit 4$i$ with a voltage level corresponding to the light amount of the reflected excitation light thus detected by actions of photoelectric conversion. The rotary filter control unit 4$i$ rotates the rotary filter 4$h$ with a predetermined revolution based upon the aforementioned luminous intensity signal. This allows variation of the transmissivity with respect to the excitation light continuously as shown in FIG. 28, for example, thereby enabling adjustment of the period in which excitation light from the laser light source 4$a$ is cast onto the subject 101.

Figure 29:
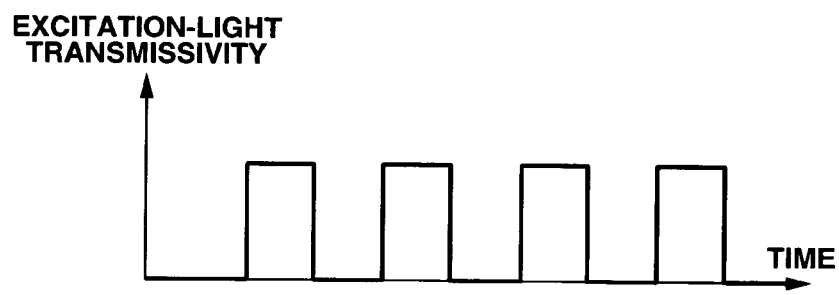
Figure 30:
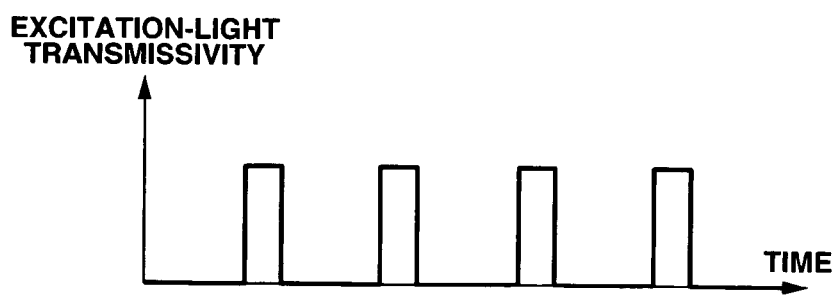

Furthermore, the image generating device 1D according to the present modification can operate in another mode as described below. In this mode, first, the rotary filter 4$h$ is rotated with the transmission filter 4$k$1 thereof inserted into the optical path for the laser light source 4$a$. Let us say that the excitation light of further excessive luminous intensity is cast onto the subject 101, for example. In this case, the PD 4$g$ detects the reflected excitation light output from the insertion unit 2 through the mirrors 4$e$ and 4$f$. Then, the PD 4$g$ outputs a luminous intensity signal to the rotary filter control unit 4$i$ with a voltage level corresponding to the light amount of the reflected excitation light thus detected by actions of photoelectric conversion. The rotary filter control unit 4$i$ rotates the rotary filter 4$k$ with a predetermined revolution and with a phase different from that of the rotary filter 4$h$ while maintaining the rotation of the rotary filter 4$h$, based upon the aforementioned luminous intensity signal. This allows variation of the transmissivity with respect to the excitation light continuously as shown in FIG. 29, for example. The excitation light, which has been output from the laser light source 4$a$ and which has passed through the rotary filters 4$h$ and 4$k$, is cast onto the subject 101 for a shorter illumination duration than those shown in FIGS. 28 and 29. The reason is that the rotary filters 4$h$ and 4$k$ rotate with generally the same predetermined revolution and with predetermined phases different from one another. That is to say, the rotary filter control unit 4$i$ performs driving control so as to rotate the rotary filters 4$h$ and 4$k$ with phases different from one another. This enables adjustment of the period in which excitation light from the laser light source 4$a$ is cast onto the subject 101.

Figure 31:
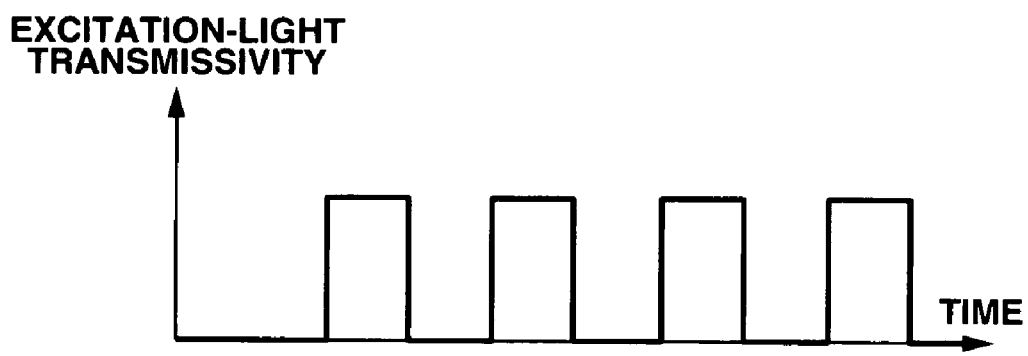
Figure 32:
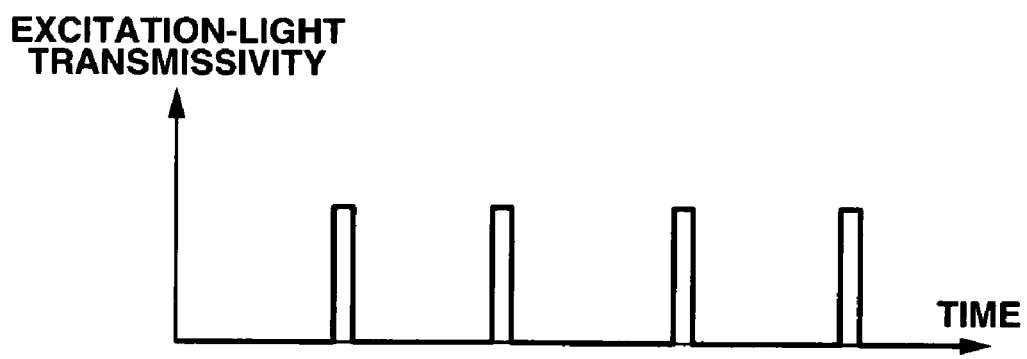

Note that with the image generating device 1D according to the present modification, the rotary filter control unit 4$i$ changes the phase of the rotary filter 4$k$, thereby enabling control of the period in which excitation light from the laser light source 4$a$ is cast onto the subject 101. For example, let us say that the rotary filter 4$h$ is rotated with a phase as shown in FIG. 28. Furthermore, let us say that the rotary filter 4$k$ is rotated with a phase as shown in FIG. 31. As shown in FIG. 32, the excitation light, which has been output from the laser light source 4$a$ and which has passed through the rotary filters 4$h$ and 4$k$, is cast onto the subject 101 for a shorter illumination period than those shown in FIGS. 28 and 29.

Modification 5 of Embodiment 4

Figure 33:
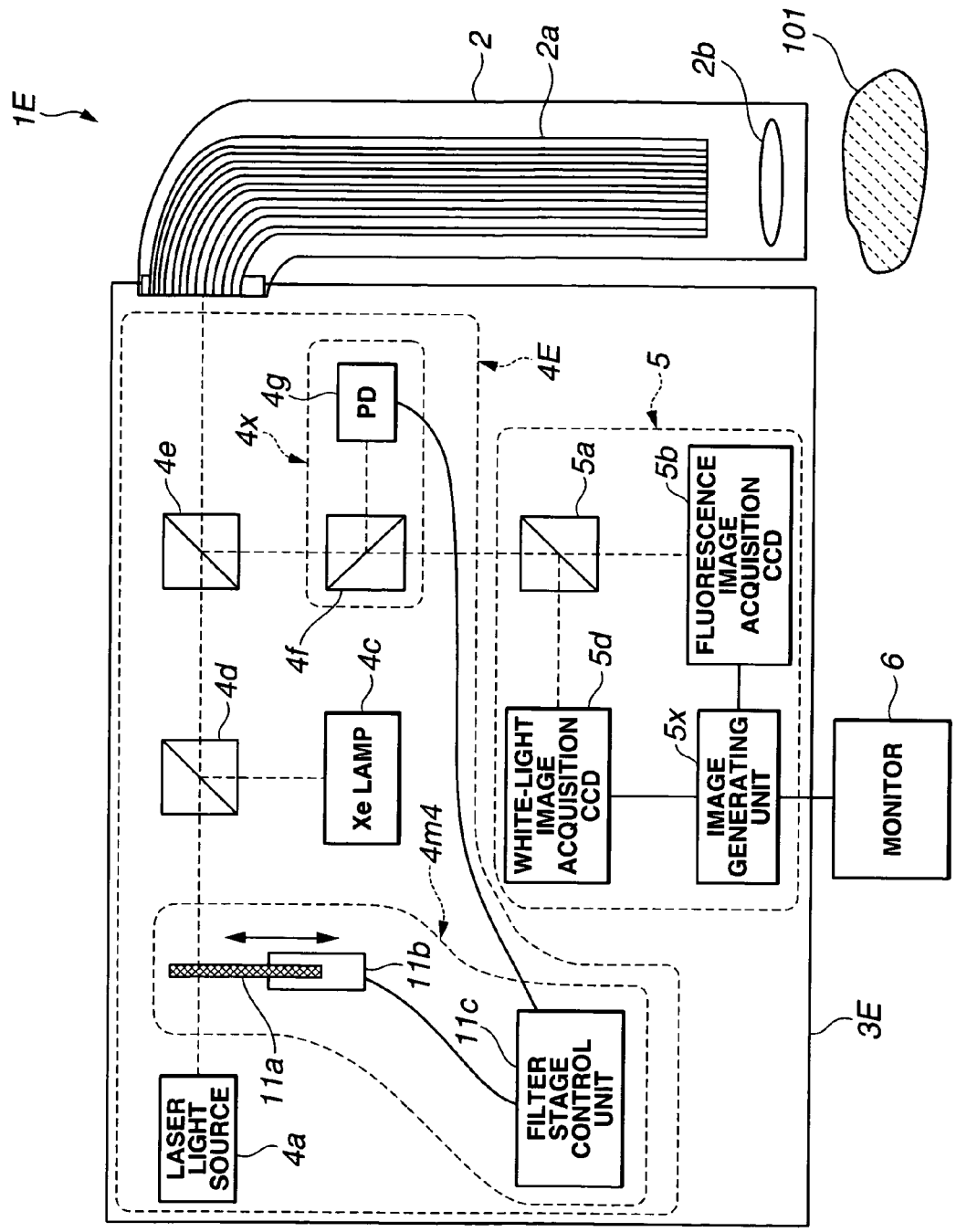

Also, a modification 5 may be made according to the present embodiment, including an illumination light adjusting unit which is a variable-transmissivity unit as shown in FIG. 33. That is to say, an image generating device 1E may comprise the insertion unit 2 having the same configuration as described above, a light source device 4E, a device main unit 3E including the processor 5 having the same configuration as described above, and the monitor 6 having the same configuration as described above.

The light source device 4E includes the laser light source 4a, the xenon lamp 4c for emitting white light, the mirrors 4d and 4e, the luminous intensity detecting unit 4x, and an illumination light adjusting unit 4m4. Furthermore, the illumination light adjusting unit 4m4 comprises a filter 11a, a filter stage 11b, and a filter stage control unit 11c. That is to say, the light source device 4E has generally the same configuration as that of the light source device 4 described above, except for including the filter 11a, the filter stage 11b, and the filter stage control unit 11c, instead of the laser driving unit 4b.

The filter 11a which is a variable-transmissivity unit has a function of shielding the excitation light output from the laser light source 4a. Furthermore, with such a configuration, the filter 11a is driven by the filter stage 11b so as to be inserted into the illumination optical path for the laser light source 4a in an on/off manner.

The filter stage 11b allows reciprocating motion of the filter 11a along an axis orthogonal to the illumination optical path for the laser light source 4a according to the control signal output from the filter stage control unit 11c.

The filter stage control unit 11c outputs a control signal to the filter stage 11b based upon the luminous intensity signal output from the luminous intensity detecting unit 4x, thereby enabling driving control of the filter 11a.

The image generating device 1E according to the present modification can operate in a mode as described below. Let us say that the excitation light of excessive luminous intensity is cast onto the subject 101, for example. In this case, the PD 4g detects the reflected excitation light output from the insertion unit 2 through the mirrors 4e and 4f. Then, the PD 4g outputs a luminous intensity signal to the filter stage control unit 11c with a voltage level corresponding to the light amount of the reflected excitation light thus detected by actions of photoelectric conversion. The filter stage control unit 11c outputs a control signal to the filter stage 11b based upon the aforementioned luminous intensity signal. The filter stage 11b effects reciprocating motion of the filter 11a along an axis orthogonal to the illumination optical path for the laser light source 4a according to the aforementioned control signal. Thus, the filter 11a is inserted into the illumination optical path for the laser light source 4a in an on/off manner. As a result, the present modification allows continuous variation of the transmissivity for the excitation light as shown in FIG. 28, for example. This enables control of the period in which excitation light from the laser light source 4a is cast onto the subject 101.

Modification 6 of Embodiment 4

Figure 34:
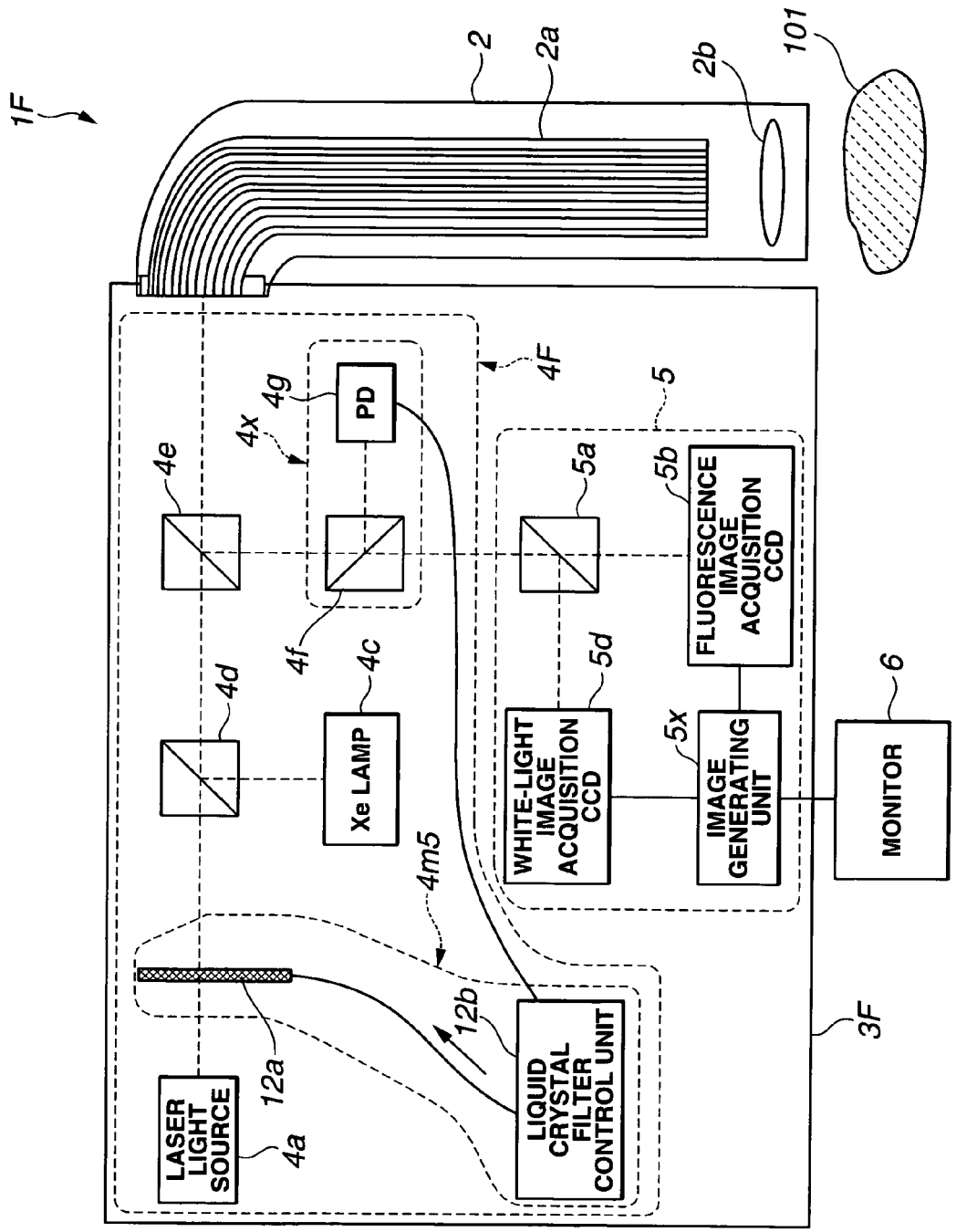

Also, a modification 6 may be made according to the present embodiment, including an illumination light adjusting unit which is a variable-transmissivity unit as shown in FIG. 34. That is to say, an image generating device 1F may comprise the insertion unit 2 having the same configuration as described above, a light source device 4F, a device main unit 3F including the processor 5 having the same configuration as described above, and the monitor 6 having the same configuration as described above.

The light source device 4F includes the laser light source 4a, the xenon lamp 4c for emitting white light, the mirrors 4d and 4e, the luminous intensity detecting unit 4x, and an illumination light adjusting unit 4m5. Furthermore, the illumination light adjusting unit 4m5 comprises a liquid crystal filter 12a and a liquid crystal filter control unit 12b. That is to say, the light source device 4F has generally the same configuration as that of the light source device 4 described above, except for including the liquid crystal filter 12a and the liquid crystal filter control unit 12b, instead of the laser driving unit 4b.

The liquid crystal filter 12a which is a variable-transmissivity unit is provided in the illumination optical path for the laser light source 4a. The liquid crystal filter 12a is driven according to a control signal output from the liquid crystal filter control unit 12b. Specifically, the orientation of the liquid crystal is controlled according to the control signal, thereby enabling variation of the transmissivity of the liquid crystal filter 12a with respect to the wavelength range of the excitation light emitted from the laser light source 4a.

The liquid crystal filter control unit 12b performs driving control of the liquid crystal filter 12a based upon the luminous intensity signal output from the luminous intensity detecting unit 4x.

The image generating device 1F according to the present modification can operate in a mode as described below. Let us say that the excitation light of excessive luminous intensity is cast onto the subject 101, for example. In this case, the PD 4g detects the reflected excitation light output from the insertion unit 2 through the mirrors 4e and 4f. Then, the PD 4g outputs a luminous intensity signal to the liquid crystal filter control unit 12b with a voltage level corresponding to the light amount of the reflected excitation light thus detected by actions of photoelectric conversion. The liquid crystal filter control unit 12b controls the orientation of the liquid crystal of the liquid crystal filter 12a based upon the aforementioned luminous intensity signal. This enables variation of the transmissivity with respect to the excitation light continuously as shown in FIG. 28, for example, thereby enabling adjustment of the period in which excitation light from the laser light source 4a is cast onto the subject 101.

With each of the image generating devices 1 and 1A, the PD 4g detects the reflected excitation light output from the insertion unit 2, and outputs a luminous intensity signal corresponding to the light amount of the reflected excitation light thus detected, to the laser driving unit 4b which is a light source output adjusting unit. This enables adjustment of the luminous intensity of the excitation light emitted from the laser light source 4a. Thus, each of the image generating devices 1 and 1A according to the present embodiment allows observation of the subject, i.e., a tissue which is to be observed within the living body while preventing the excitation light of excessive luminous intensity from being cast onto the subject by the laser light source 4a. This suppresses fading of the fluorescent dye as much as possible. This allows the operator to make fluorescence observation for an extended period of time.

On the other hand, with each of the image generating devices 1B, 1C, 1D, 1E, and 1F, the PD 4g detects the reflected excitation light output from the insertion unit 2, and outputs a luminous intensity signal corresponding to the light amount of the reflected excitation light thus detected, to the variable-transmissivity unit thereof. This enables adjustment of the luminous intensity or the illumination duration of the excitation light emitted from the laser light source 4a. Thus, the image generating devices 1B, 1C, 1D, 1E, and 1F, each of which is a modification according to the present embodiment, have the same advantages as those of the image generating devices 1 and 1A. Furthermore, each of the aforementioned modifications controls luminous intensity without direct control of the laser light source 4a. Thus, the aforementioned modifications have the advantage of enabling fluorescence observation while suppressing aging of the laser light source 4a, in addition to the advantages of the image generating devices 1 and 1A.

Embodiment 5

The embodiment 5 has generally the same configuration as that of the embodiment 4. Accordingly, description will be made regarding only components that differ between these embodiments. On the other hand, the same components are denoted by the same reference numerals, and description thereof will be omitted.

Figure 35:
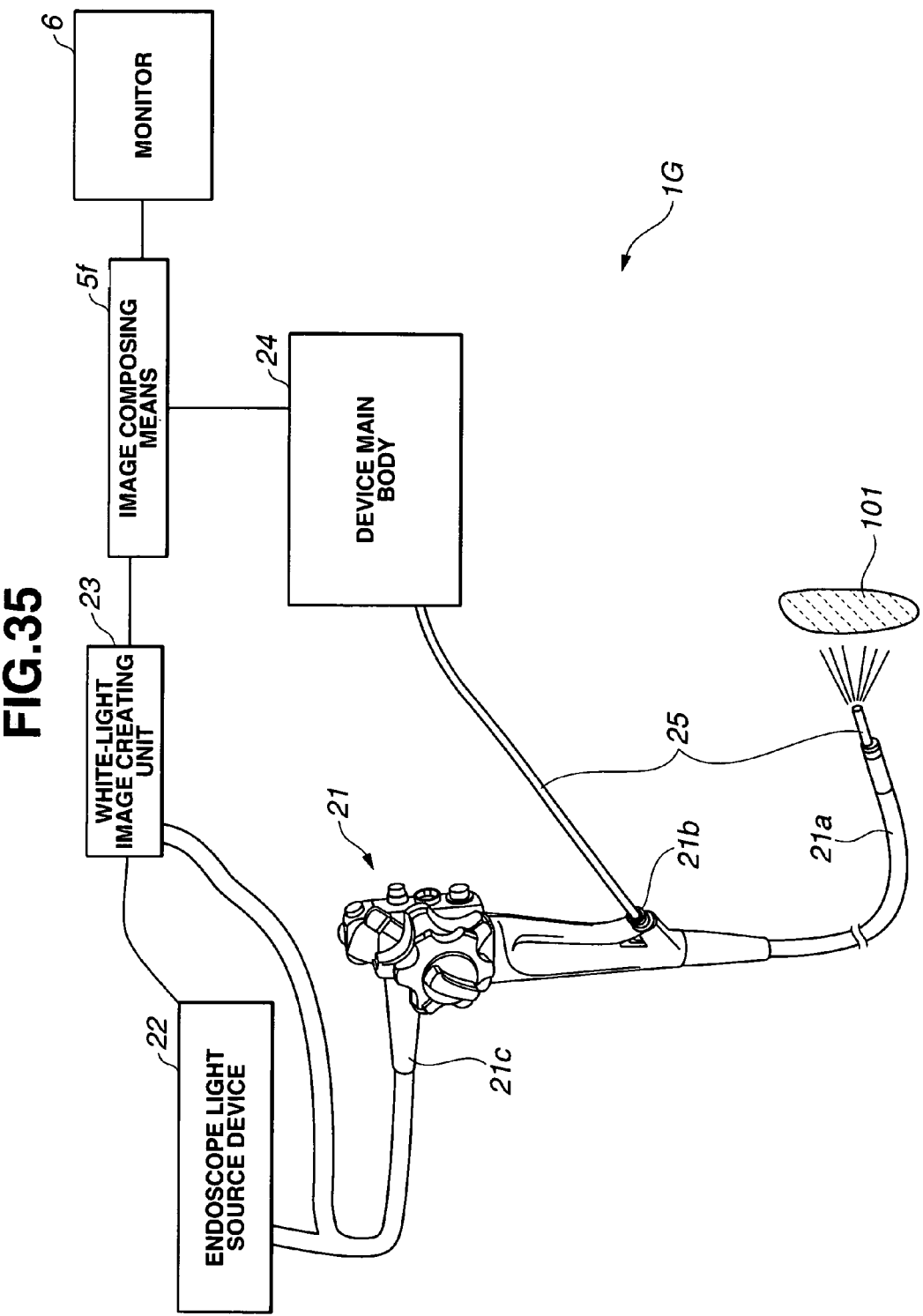
FIGS. 35 and 36 relate to an embodiment 5 according to, the present invention.

An image generating device 1G according to the present embodiment comprises the image composing unit 5f, the monitor 6, an endoscope 21, an endoscope light source device 22, a white light image generating unit 23, a device main unit 24, and a probe 25, as shown in FIG. 35. Here, the white light image generating unit 23 comprises the aforementioned white light image acquisition CCD 5d and image generating unit 5e. Note that the white light image acquisition CCD 5d and the image generating unit 5e are not shown in FIG. 35.

The endoscope 21 includes an endoscope insertion unit 21a formed with a size, shape, and flexibility to allow insertion thereof into the body cavity. The endoscope insertion unit 21a has an unshown tubular therapeutic instrument inserting channel which passes through the inside thereof. One end of the therapeutic instrument inserting channel communicates with a therapeutic instrument inserting portion 21b provided on the proximal end of the endoscope insertion unit 21a. On the other hand, the other end of the therapeutic instrument inserting channel communicates with an unshown opening provided on the distal end of the endoscope insertion unit 21a. Furthermore, the endoscope 21 includes a universal cable 21c. The endoscope 21 has a function of casting white light output from the endoscope light source device 22 onto the subject 101, as well as having a function of introducing the reflected white light, which is white light reflected by the subject 101, to the endoscope light source device 22 and the white light image generating unit 23, through the universal cable 21c.

The endoscope light source device 22 which is a white light source emits white light onto the endoscope 21. Furthermore, the endoscope light source device 22 is connected to the white light image generating unit 23, and outputs a timing signal to the white light image generating unit 23 with the time of detection of the reflected white light output from the endoscope 21 in order to notify the white light image generating unit 23 of the generation timing of a white light image.

The white light image generating unit 23 generates a white light image at the image generating unit 5e based upon the reflected white light which is reflected white light cast from the endoscope 21 and which is detected by the white light image acquisition CCD 5d and the timing signal output from the endoscope light source device 22. The white light image thus generated is output to the aforementioned image composing unit 5f.

Figure 36:
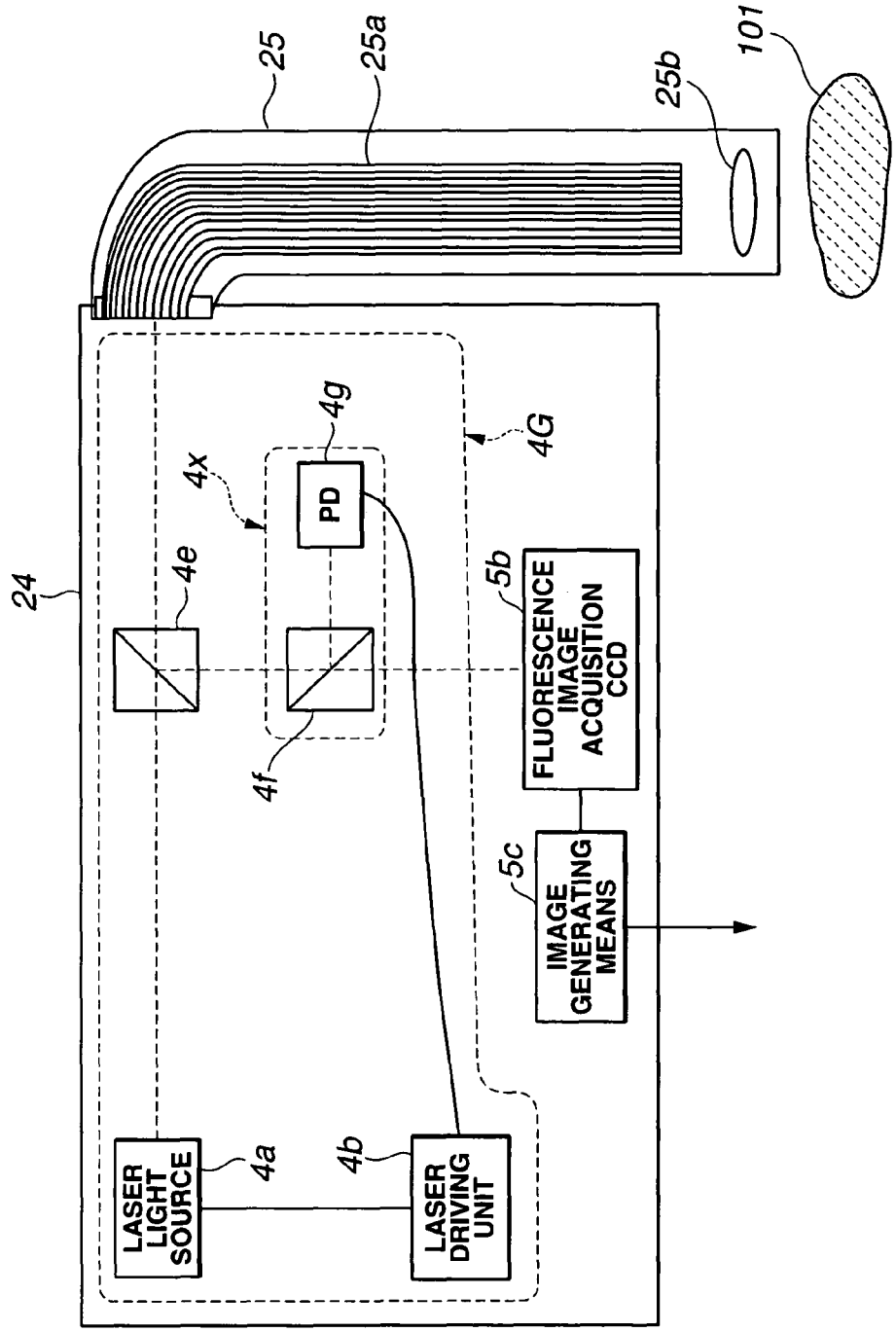

The device main unit 24 comprises a light source device 4G, the fluorescence image acquisition CCD 5d, and an image generating unit 5c, as shown in FIG. 36. Furthermore, the light source device 4G comprises the laser light source 4a, the laser driving unit 4b, the mirror 4e, and the luminous intensity detecting unit 4x. Note that the luminous intensity detecting unit 4x comprises the mirror 4f and the PD 4g.

The probe 25 has a configuration which allows detachable mounting thereof to the device main unit 24, and comprises a light introducing portion 25a which passes through the inside thereof, and an object optical system 25b provided on the distal end thereof, as shown in FIG. 36.

The light introducing portion 25a is formed of quartz fibers or the like, and has a function serving as a first light introducing portion for introducing the excitation light emitted from the light source device 4G to the subject 101, i.e., each organ within the living body, as well as having a function serving as a second light introducing portion for introducing the fluorescence emitted from the subject 101 due to the excitation light cast from the light source device 4G to the device main unit 24. Furthermore, the light introducing portion 25a has a function of introducing the reflected excitation light, which is the excitation light output from the light source device 4G and which is reflected by the subject 101, to the device main unit 24.

The object optical system 25b casts the excitation light output from the light introducing portion 25a onto the subject 101. Furthermore, the object optical system 25b condenses and emits the fluorescence emitted from the subject 101 and the reflected excitation light reflected by the subject 101 onto the light introducing portion 25a.

Next, description will be made regarding observation of the tissue within the living body using the image generating device 1G according to the present embodiment with reference to FIGS. 35 and 36.

In observation of the living body using the image generating device 1G, first, the operator connects the probe 25 to the device main unit 24. Subsequently, the operator inserts the probe 25 into the therapeutic instrument inserting portion 21b of the endoscope 21 so that the probe 25 passes through the therapeutic instrument channel, and the end thereof protrudes from the unshown opening provided on the distal end of the endoscope insertion unit 21a. Then, the operator inserts the endoscope insertion unit 21a of the endoscope 21 in such a state into the body cavity, following which the operator turns on the power supply for the laser light source 4a and the endoscope light source device 22, whereupon light is emitted from the laser light source 4a and the endoscope light source device 22. Subsequently, the operator inserts the probe 25 into the vicinity of the desired portion within the living body which is to be observed and which has been administered with a fluorescent material for fluorescence observation so as to display an image of the subject 101 on the monitor 6. Let us say that the distal end of the probe 25 comes in contact with the subject 101 in such observation, for example. In some cases, this leads to the excitation light of excessive luminous intensity cast onto the subject 101. The present embodiment handles such a situation as follows. The PD 4g which is a component of the luminous intensity detecting unit 4x detects the reflected excitation light output from the probe 25 through the mirrors 4e and 4f. Then, the PD 4g outputs a luminous intensity signal to the laser driving unit 4b with a voltage level corresponding to the light amount of the reflected excitation light thus detected by actions of photoelectric conversion. The laser driving unit 4b which is an illumination light adjusting unit, i.e., a light source output adjusting unit varies the amount of the driving current output to the laser light source 4a based upon the aforementioned luminous intensity signal, thereby adjusting the luminous intensity of the excitation light.

Note that examples employed as the adjustment method for the luminous intensity of the excitation light include the methods as described in the embodiment 4 with reference to FIGS. 16 and 17. Furthermore, the methods may be employed as shown in FIGS. 18 and 19 in which a threshold is set.

The image generating device 1G according to the present embodiment has the same advantages as those of the image generating device 1 according to the embodiment 4 as described above. Furthermore, the image generating device 1G according to the present embodiment includes the device main unit 24 having a simple configuration as compared with the device main unit 3. Thus, the image generating device 1G provides the same advantages as those of the image generating device 1 according to the embodiment 4 at lower cost than that of the image generating device 1.

Embodiment 6

An embodiment 6 has generally the same configuration as that of the embodiment 4. Accordingly, description will be made regarding only components that differ between these embodiments. On the other hand, the same components are denoted by the same reference numerals, and description thereof will be omitted.

Figure 37:
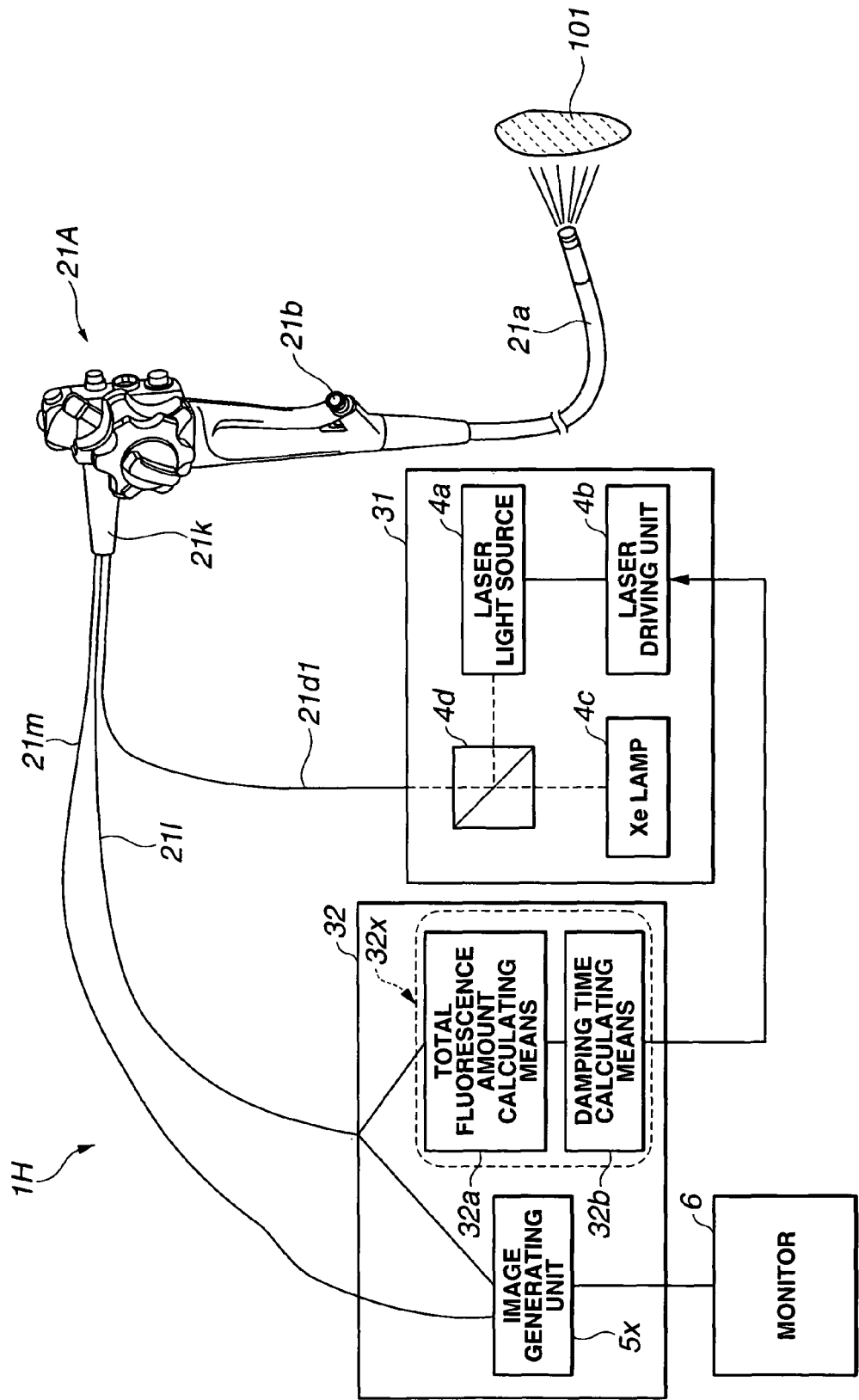
FIGS. 37 through 41 relate to an embodiment 6 according to the present invention.

An image generating device 1H according to the present embodiment comprises an endoscope 21A, a light source device 31, a device main unit 32, and the monitor 6, as shown in FIG. 37.

The light source device 31 comprises the laser light source 4a, the laser driving unit 4b, the xenon lamp 4c for emitting white light, and the mirror 4d. The light source device 31 has a function of casting excitation light and white light onto the subject 101 through the endoscope 21A.

Figure 38:
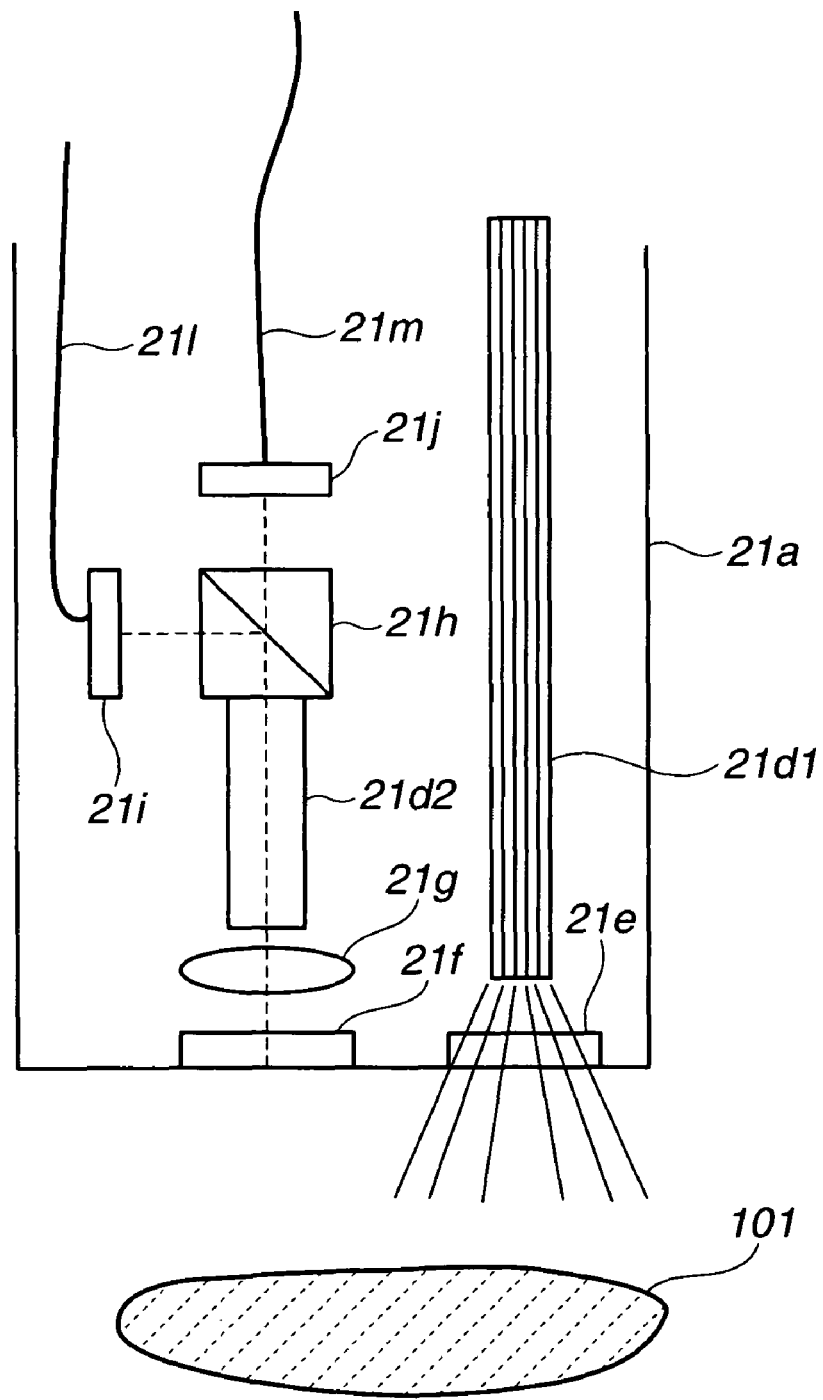

The endoscope 21A comprises the endoscope insertion unit 21a, the therapeutic instrument inserting portion 21b, and a universal cable 21k. The endoscope insertion unit 21a includes a light introducing portion 21d1 which passes through the inside thereof. Furthermore, the endoscope insertion unit 21a includes an object optical systems 21e and 21g, an optical filter 21f, a mirror 21h, a fluorescence acquisition CCD 21i, and a white light acquisition CCD 21j, at the distal end thereof, as shown in FIG. 38. Furthermore, the endoscope insertion unit 21a includes a light introducing portion 21d2 between the object optical system 21g and the mirror 21h.

The light introducing portion 21d1, which is a first light introducing portion, is formed of quartz fibers or the like, and passes through the portion from the endoscope insertion unit 21a up to the universal cable 21k within the endoscope 21A. Furthermore, the light introducing portion 21d1 is provided so as to connect the universal cable 21k and the light source device 31 outside of the endoscope 21A. With such a configuration, the excitation light and the white light output from the light source device 31 are introduced to the subject 101, i.e., each organ within the living body, through the endoscope 21A. On the other hand, the light introducing portion 21d2 which is a second light introducing portion is formed of quartz fibers or the like. The light introducing portion 21d2 has a function of introducing the fluorescence emitted from the subject 101 due to the excitation light cast from the light source device 31, to the fluorescence acquisition CCD 21i through the mirror 21h. Furthermore, the light introducing portion 21d2 has another function of introducing the reflected white light, which is white light emitted from the light source device 31 and reflected by the subject 101, to the white light acquisition CCD 21j.

The object optical system 21e has a function of casting the excitation light and the white light output from the light introducing portion 21d1, onto the subject 101.

The optical filter 21f has a function of allowing the fluorescence emitted from the subject 101 and the reflected white light reflected by the subject 101 to pass therethrough, as well as having a function of shielding the reflected excitation light. The fluorescence and the reflected white light, which have passed through the optical filter 21f, are output to the object optical system 21g.

The object optical system 21g condenses the fluorescence and the reflected white light output from the optical filter 21f, and emits onto the light introducing portion 21d2.

The mirror 21h has a function of allowing the reflected white light to pass therethrough, as well as having a function of reflecting the fluorescence. These functions enables separation of the input light introduced by the light introducing portion 21d2 into the fluorescence and the reflected white light.

The fluorescence acquisition CCD 21i which is a first light detecting unit detects the fluorescence output from the mirror 21h, and converts the detected fluorescence into a fluorescence image signal. The fluorescence image signal is output to the image generating block unit 5x provided within the device main unit 32 through a signal line 21l. Furthermore, the fluorescence acquisition CCD 21i detects the fluorescence output from the mirror 21h, and converts the detected information regarding the fluorescence amount into a signal in the form of a fluorescence amount signal. The fluorescence amount signal is output to the device main unit 32 through the signal line 21l.

The signal line 21l passes through the portion from the fluorescence acquisition CCD 21i up to the universal cable 21k within the endoscope 21A. Furthermore, the signal line 21l is provided so as to connect the universal cable 21k and the device main unit 32 outside of the endoscope 21A.

The white light acquisition CCD 21j which is a second light detecting unit detects the reflected white light output from the mirror 21h, and converts the reflected white light thus detected, into a white light image signal. The white light image signal is output to the image generating block unit 5x provided within the device main unit 32 through a signal line 21m.

The signal line 21m passes through the portion from the white light acquisition CCD 21j up to the universal cable 21k within the endoscope 21A. Furthermore, the signal line 21m is provided so as to connect the universal cable 21k and the device main unit 32 outside of the endoscope 21A.

The universal cable 21k is provided so as to communicate with the proximal end of the endoscope insertion unit 21a. The universal cable 21k includes the light introducing portion 21d1, the signal line 21l, the signal line 21m, and so forth, in the form of a bundle therewithin.

The device main unit 32 includes the image generating block unit 5x and a luminous intensity detecting unit 32x. Here, the luminous intensity detecting unit 32x comprises a total fluorescence amount calculating unit 32a and a damping time calculating unit 32b.

The total fluorescence amount calculating unit 32a calculates the total amount of the fluorescence emitted from the subject 101 based upon the fluorescence amount signal output from the fluorescence acquisition CCD 21i, and converts the data of the total fluorescence amount thus calculated, into a signal in the form of a total fluorescence amount signal. The total fluorescence amount signal is output to the damping time calculating unit 32b.

The damping time calculating unit 32b calculates the damping time constant which is a period of time for which the total fluorescence amount emitted from the subject 101 at a predetermined point decreases up to a predetermined total fluorescence amount. A control signal generated based upon the calculated damping time constant is output to the laser driving unit 4b.

That is to say, the luminous intensity detecting unit 32x performs processing at the total fluorescence amount calculating unit 32a and the damping time calculating unit 32b based upon the fluorescence amount signal representing the fluorescence amount emitted from the subject as described above. Subsequently, the luminous intensity detecting unit 32x outputs the control signal corresponding to the fluorescence amount signal, to the laser driving unit 4b which is an illumination light adjusting unit.

Next, description will be made regarding observation of the tissue within the living body using the image generating device 1H according to the present embodiment with reference to FIGS. 37 through 41.

In observation of the living body using the image generating device 1H, first, the operator inserts the endoscope insertion unit 21a of the endoscope 21A into the body cavity, following which the operator turns on the power supply for the laser light source 4a and the xenon lamp 4c, whereupon light is emitted from the laser light source 4a and the xenon lamp 4c. Subsequently, the operator inserts the endoscope insertion unit 21a into the vicinity of the desired portion which is to be observed and which has been administered with a fluorescent material for fluorescence observation so as to display an image of the subject 101 on the monitor 6. Let us say that the distal end of the endoscope insertion unit 21a is inserted around a position where the distal end thereof might come in contact with the subject 101 in such observation, for example. In some cases, this leads to excitation light of excessive luminous intensity cast onto the subject 101. The present embodiment handles such a situation as follows. The fluorescence acquisition CCD 21i detects the fluorescence output from the mirror 21h (Step S1 in FIG. 41). The fluorescence acquisition CCD 21i converts the information regarding the fluorescence amount thus detected, into a signal in the form of a fluorescence amount signal, following which the fluorescence acquisition CCD 21i outputs the fluorescence amount signal to the luminous intensity detecting unit 32x of the device main unit 32 through the signal line 21l. The total fluorescence amount calculating unit 32a of the luminous intensity detecting unit 32x calculates the total fluorescence amount emitted from the subject 101 based upon the fluorescence amount signal output from the fluorescence acquisition CCD 21i (Step S2 in FIG. 41). The total fluorescence amount calculating unit 32a converts the data of the total fluorescence amount thus calculated, into a signal in the form of a total fluorescence signal, and outputs the total fluorescence amount signal to the damping time calculating unit 32b.

Figure 41:
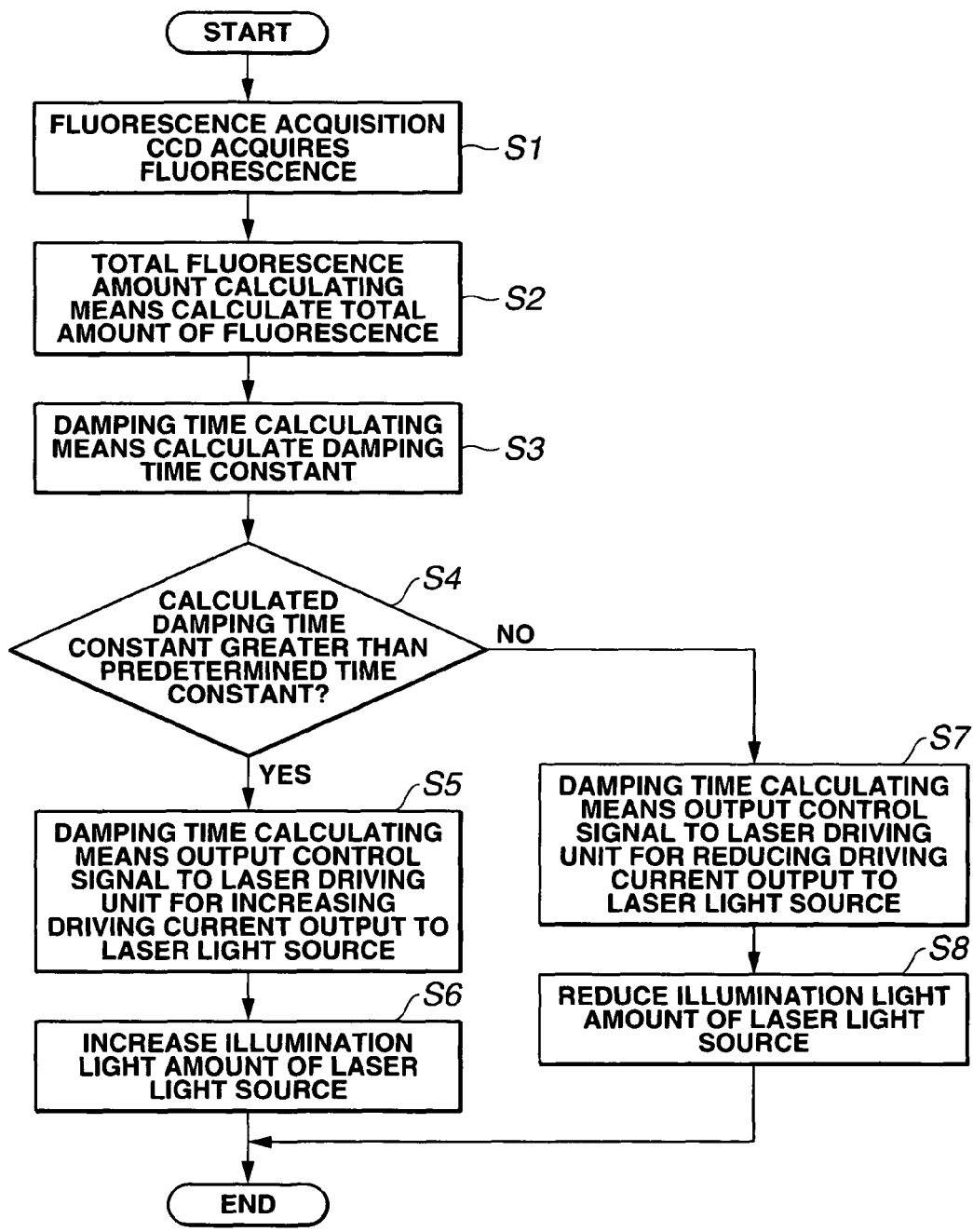

The damping time calculating unit 32b calculates the damping time constant in a situation in which the distal end of the endoscope insertion unit 21a is inserted at a predetermined position, based upon the total fluorescence signal output from the total fluorescence calculating unit 32a (Step S3 in FIG. 41).

Figure 39:
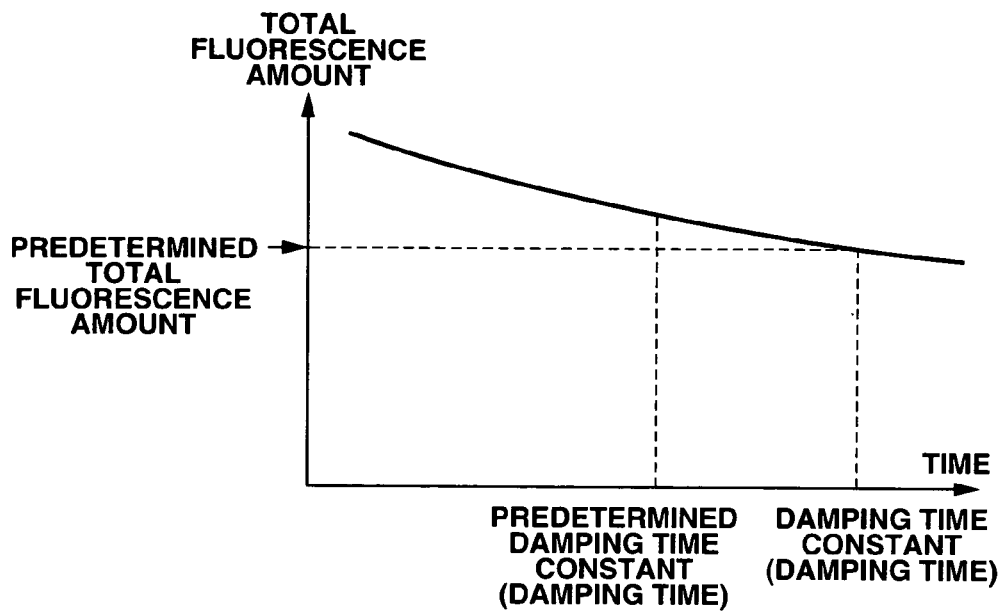

Then, in a case that the damping time constant calculated based upon the total fluorescence signal is greater than a predetermined time constant which is a predetermined threshold set in the damping time calculating unit 32b beforehand as shown in FIG. 39, for example, the damping time calculating unit 32b determines that the luminous intensity of the excitation light is insufficient (Step S4 in FIG. 41), and outputs a control signal to the laser driving unit 4b so that the damping time constant thus calculated becomes generally equal to the predetermined time constant. As a result, the laser driving unit 4b raises the driving current amount output to the laser light source 4a based upon the aforementioned control signal, thereby increasing the luminous intensity of the excitation light (Steps S5 and S6 in FIG. 41).

Figure 40:
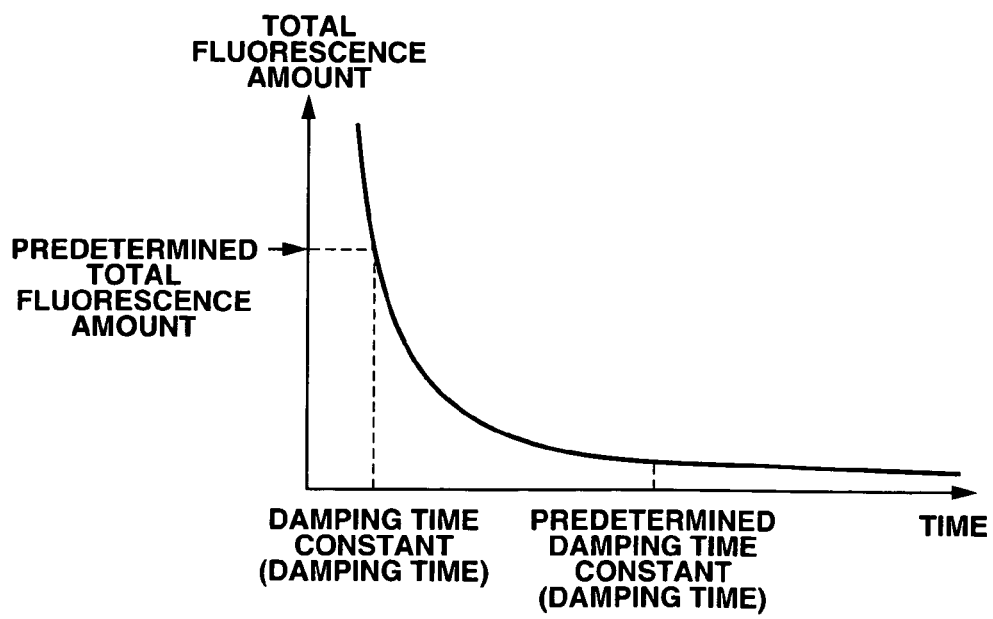

On the other hand, in a case that the damping time constant calculated based upon the total fluorescence signal is smaller than a predetermined time constant which is a predetermined threshold set in the damping time calculating unit 32b beforehand as shown in FIG. 40, for example, the damping time calculating unit 32b determines that the excitation light of excessive luminous intensity has been cast (Step S4 in FIG. 41), and outputs a control signal to the laser driving unit 4b so that the damping time constant thus calculated becomes generally equal to the predetermined time constant. As a result, the laser driving unit 4b reduces the driving current amount output to the laser light source 4a based upon the aforementioned control signal, thereby reducing the luminous intensity of the excitation light (Steps S7 and S8 in FIG. 41).

The image generating device 1H according to the present embodiment has the same advantages as those of the image generating device 1 according to the embodiment 4 as described above. Furthermore, the image generating device 1H according to the present embodiment includes the device main unit 32 having a simple configuration as compared with the device main unit 3. Thus, the image generating device 1H provides the same advantages as those of the image generating device 1 according to the embodiment 4 at lower cost than that of the image generating device 1.

It should be understood that the present invention is not intended to be limited to the embodiments described above; rather, various changes and modifications may be made without departing from the essence of the present invention.

It is clear that a wide variety of embodiments may be made based upon the present invention without departing from the spirit and scope of the invention. The present invention is not to be restricted by particular embodiments except as limited by the appended Claims.

What is claimed is:

1. An image generating device comprising:
an excitation light emission unit for emitting excitation light with a predetermined wavelength;
a white light source for emitting white light;
a first light introducing unit for introducing the excitation light to a subject;
a second light introducing unit for introducing the white light to the subject;
an excitation light scanning unit for scanning the excitation light introduced by the first light introducing unit onto a predetermined region within an illumination region in the subject to which the white light is introduced;
a light condensing unit disposed between the excitation light scanning unit and the subject for condensing the excitation light onto the subject;
a reflected white light photoreceptor unit for receiving the reflected light due to the white light from the subject; and
a fluorescence photoreceptor unit for receiving fluorescence excited in the subject due to the excitation light,
wherein the excitation light scanning unit includes an x-axis scanning portion for scanning the excitation light in an x-axis direction and a y-axis scanning portion for scanning the excitation light in a y-axis direction.

2. An image generating device according to claim 1, further comprising:
an observation image generating unit for generating an observation image of the subject based upon a received light signal received by the reflected white light photoreceptor unit;

a fluorescence image generating unit for generating a fluorescence image of the subject based upon a received light signal received by the fluorescence photoreceptor unit; and an image composing unit for composing the observation image and the fluorescence image into a single image.

3. An image generating device according to claim 1, wherein the excitation light emission unit comprises a laser light source.

4. An image generating device according to claim 1, wherein at least the first light introducing unit, the second light introducing unit, the excitation light scanning unit, and the light condensing unit are included within an insertion unit which can be inserted into a body cavity.

5. An image generating device according to claim 1, wherein the light condensing unit includes a light-condensing-level variation unit for varying the condensing level to a desired level for casting excitation light emitted from the excitation light emission unit onto the subject.

6. An image generating device according to claim 1, further including an insertion unit having sufficient flexibility to allow insertion thereof into a body cavity,
wherein at least a part of the first light introducing unit, at least a part of the second light introducing unit, the excitation light scanning unit, and the light condensing unit are included in the insertion unit.

7. An image generating device comprising:
an excitation light emission unit for emitting excitation light with a predetermined wavelength;
a white light source for emitting white light;
a first light introducing unit for introducing the excitation light to a subject;
a second light introducing unit for introducing the white light to the subject;
an excitation light scanning unit for scanning the excitation light introduced by the first light introducing unit onto a predetermined region within an illumination region in the subject to which the white light is introduced;
a light condensing unit disposed between the excitation light scanning unit and the subject for condensing the excitation light onto the subject;

a reflected white light photoreceptor unit for receiving the reflected light due to the white light from the subject; and
a fluorescence photoreceptor unit for receiving fluorescence excited in the subject due to the excitation light,
wherein the light condensing unit includes a light-condensing-level variation unit for varying the condensing level to a desired level for casting excitation light emitted from the excitation light emission unit onto the subject, and the light-condensing-level variation unit is a shape-variable mirror.

8. An image generating device according to claim 7, further comprising:
an observation image generating unit for generating an observation image of the subject based upon a received light signal received by the reflected white light photoreceptor unit;
a fluorescence image generating unit for generating a fluorescence image of the subject based upon a received light signal received by the fluorescence photoreceptor unit; and
an image composing unit for composing the observation image and the fluorescence image into a single image.

9. An image generating device according to claim 7, wherein the excitation light emission unit comprises a laser light source.

10. An image generating device according to claim 7, wherein at least the first light introducing unit, the second light introducing unit, the excitation light scanning unit, and the light condensing unit are included within an insertion unit which can be inserted into a body cavity.

11. An image generating device according to claim 7, further including an insertion unit having sufficient flexibility to allow insertion thereof into a body cavity, wherein at least a part of the first light introducing unit, at least a part of the second light introducing unit, the excitation light scanning unit, and the light condensing unit are included in the insertion unit.

* * * * *